United States Patent
Daly et al.

(10) Patent No.: US 8,648,006 B2
(45) Date of Patent: Feb. 11, 2014

(54) ELECTROLESS PLATING IN MICROCHANNELS

(75) Inventors: Francis P. Daly, Delaware, OH (US); Richard Long, New Albany, OH (US); Junko Ida, Tokyo (JP); Rachid Taha, Dublin, OH (US); Terry Mazanec, Solon, OH (US); Barry L. Yang, Dublin, OH (US)

(73) Assignee: Velocys, Inc., Plain City, OH (US)

( * ) Notice: Subject to any disclaimer, the term of this patent is extended or adjusted under 35 U.S.C. 154(b) by 1520 days.

(21) Appl. No.: 11/549,625

(22) Filed: Oct. 13, 2006

(65) Prior Publication Data

US 2008/0214884 A1 Sep. 4, 2008

Related U.S. Application Data

(60) Provisional application No. 60/727,112, filed on Oct. 13, 2005, provisional application No. 60/726,733, filed on Oct. 13, 2005.

(51) Int. Cl.
*B01J 23/42* (2006.01)
*B01J 23/46* (2006.01)
*B01J 8/02* (2006.01)

(52) U.S. Cl.
USPC .................. 502/325; 423/245.3; 422/211

(58) Field of Classification Search
USPC ........ 423/245.3; 502/325, 332, 334; 585/652; 431/268; 422/122, 139, 171, 177, 190, 422/211
See application file for complete search history.

(56) References Cited

U.S. PATENT DOCUMENTS

| 4,088,435 | A | * | 5/1978 | Hindin et al. .................. 431/7 |
|---|---|---|---|---|
| 4,251,391 | A | | 2/1981 | Mauldin et al. |
| 4,585,752 | A | * | 4/1986 | Ernest ......................... 502/304 |
| 4,711,009 | A | * | 12/1987 | Cornelison et al. ............ 29/890 |
| 4,892,857 | A | | 1/1990 | Tennant et al. |
| 5,041,407 | A | | 8/1991 | Williamson et al. |
| 5,250,489 | A | | 10/1993 | Dalla Betta et al. |
| 5,281,128 | A | | 1/1994 | Dalla Betta et al. |
| 5,298,280 | A | | 3/1994 | Kaczur et al. |
| 5,425,632 | A | | 6/1995 | Tsurumi et al. |
| 5,474,441 | A | | 12/1995 | Farrauto et al. |
| 5,500,315 | A | | 3/1996 | Calvert et al. |
| 5,916,505 | A | | 6/1999 | Cisar et al. |
| 5,948,377 | A | | 9/1999 | Sung |
| 5,958,828 | A | | 9/1999 | Murkami et al. |
| 6,071,554 | A | | 6/2000 | Isomura et al. |

(Continued)

FOREIGN PATENT DOCUMENTS

| EP | 0781590 | 7/1997 |
|---|---|---|
| EP | 1035229 | 3/2004 |
| JP | 58204168 | 11/1983 |
| JP | 05222543 | 8/1993 |

OTHER PUBLICATIONS

Suzuki et al. Development of micro catalytic combustor with Pt/Al2O3 thin films. JSME International Journal, Series B, vol. 47, No. 3 (2004) 522-527.*

(Continued)

*Primary Examiner* — Katherine Zalasky
(74) *Attorney, Agent, or Firm* — Frank Rosenberg

(57) ABSTRACT

Novel methods of electroless plating are described. Catalyst coatings can be applied within microchannel apparatus. Various reactions, including combustion and steam reforming, can be conducted over electroless catalyst coatings.

19 Claims, 2 Drawing Sheets

(56) References Cited

U.S. PATENT DOCUMENTS

| | | | |
|---|---|---|---|
| 6,117,578 | A | 9/2000 | Lesieur |
| 6,284,210 | B1 | 9/2001 | Euzen et al. |
| 6,329,434 | B1* | 12/2001 | Wen et al. .............. 518/703 |
| 6,488,838 | B1* | 12/2002 | Tonkovich et al. ......... 208/108 |
| 6,488,907 | B1 | 12/2002 | Barnes et al. |
| 6,706,420 | B1* | 3/2004 | Kozlov et al. .............. 428/668 |
| 6,916,943 | B2* | 7/2005 | Addiego et al. .............. 554/141 |
| 7,186,388 | B2 | 3/2007 | Bowe et al. |
| 2002/0031471 | A1 | 3/2002 | Tonkovich et al. |
| 2003/0144366 | A1 | 7/2003 | Daage et al. |
| 2003/0202916 | A1* | 10/2003 | Liu et al. .............. 422/177 |
| 2004/0175317 | A1 | 9/2004 | Yang et al. |
| 2005/0176580 | A1 | 8/2005 | Osaka et al. |
| 2005/0244304 | A1 | 11/2005 | Tonkovich et al. |
| 2005/0271563 | A1 | 12/2005 | Yang et al. |
| 2005/0272965 | A1 | 12/2005 | Watson et al. |
| 2006/0083672 | A1 | 4/2006 | Daly et al. |
| 2006/0083675 | A1 | 4/2006 | Daly et al. |

OTHER PUBLICATIONS

Zanfir et al. Modelling of a catalytic plate reactor for dehydrogenation-combustion coupling. Chemical Engineering Science, vol. 56 (2001) 2671-2683.*

Zanfir et al. Catalytic combustion assisted methane steam reforming in a catalytic plate reactor. Chemical Engineering Science, vol. 58 (2003) 3947-3960.*

Lyubovsky et al. Complete and partial catalytic oxidation of methane over substrates with enhanced transport properties. Catalysis Today, 83 (2003) 183-197.*

PCT/US2006/039897, Written Opinion.

PCT/US2006/039897, International Preliminary Examination Report, mailed Oct. 13, 2006.

Janicke et al., "The controlled oxidation of hydrogen from an explosive mixture of gases using a microstructured reactor/heat exchanger and Pt/Al2O3 catalyst," J. Catal. 191, 282-293 (2000).

Wolfrath et al., "Novel Membrane Reactor with Filamentous Catalytic Bed for Propane Dehydrogenation," I. Eng. Chem. Res. 2001, 40, 5234-5239.

Venkataraman et al., "Steam Reforming of Methane and Water-Gas Shift in Catalytic Wall Reactors," AIChE Journal, May 2003, 1277-1284.

Rao et al., "Chemical and electrochemical depositions of platinum group metals and their applications," Coord. Chem. Rev. 249 (2005) 613-631.

Okinata et al., "Chap 16 Electroless Plating of Platinum Group Metals," in Electroless Plating fundamentals, Mallory et al. eds. (1991) p. 421-440.

First Office Action from Corresponding Chinese Application No. 200680038248, mailed Apr. 30, 2010.

* cited by examiner

ELECTROLESS PLATING IN MICROCHANNELS

RELATED APPLICATIONS

This application claims the benefit of U.S. provisional patent application Ser. No. 60/727,112 filed 13 Oct. 2005 and U.S. provisional patent application Ser. No. 60/726,733 filed 13 Oct. 2005.

FIELD OF THE INVENTION

This invention relates to electroless plating of metals, especially in microchannel apparatus. The invention also relates to methods of conducting reactions in microchannels.

INTRODUCTION

In recent years there has been tremendous academic and commercial interest in microchannel devices. This interest has arisen due to the advantages from microtechnology including reduced size, increased productivity, the ability to size systems of any desired capacity (i.e., "number-up"), increased heat transfer, and increased mass transfer. A review of some of the work involving microreactors (a subset of microchannel apparatus) has been provided by Gavrilidis et al., "Technology And Applications Of Microengineered Reactors," Trans. IChemE, Vol. 80, Part A, pp. 3-30 (January 2002).

Despite great efforts to produce microchannel apparatus suitable for industrial use, it is still reported that, in microreaction techology, the manufacture of catalyst coatings with long-term mechanical and chemical stability remains a challenge. See Degussa ScienceNewsletter 15, 2006.

Among other advances, the invention described in this patent application shows that coatings applied electrolessly within a microchannel can demonstrate remarkably improved stability, even under extreme conditions.

Electroless coatings are generally known and there have been some reports of electroless coatings in microchannels. Electroless metal coatings have long been known and are reviewed by Mallory et al. eds., "Electroless Plating Fundamentals & Applications," American Electroplaters Society (1990) and Chepuri et al., "Chemical and electrochemical depositions of platinum group metals and their applications," Coord. Chem. Rev., vol. 249, pp. 613-631 (2005). Yekimov et al., in U.S. Pat. No. 6,361,824 reported the electroless coating of silver on microchannels through a very thin glass sheet. The microchannels could be 50 to 1000 microns (μm) in length. It was reported that the microchannels must by horizontally aligned during coating. Yekimov et al. also reported that to avoid clogging, the upper and lower surfaces of the glass plate needed to be unobstructed. Even with limiting the microchannel to these extremely short lengths, the coating of metallic silver was reported to be 30 to 50 nm thick. Tonkovich et al. in U.S. Pat. No. 6,508,862 describe examples in which an electroless layer of Pd is deposited and suggest the use in microchannels for use as a sorbent. Tonkovich et al. in US Published Patent Application Ser. No. 20050244304 describe electroless plating in microchannels.

One aspect of the present invention is improved methods of electrolessly plating Rh. Over the years, significant efforts have been made to form Rh coatings by electroless plating. German patent DE2607988 (1977) reported an example of an electroless rhodium plating bath using rhodium ammine nitrite, i.e., $(NH_3)_xRh(NO_2)_y$, hydrazine as reducing agent, and ammonium hydroxide as complexing agent. The rhodium ammine nitrite was prepared by reaction of rhodium chloride with excess sodium nitrite and ammonium hydroxide. Similarly, U.S. Pat. No. 6,455,175 (2002) reported a composition for electroless Rh plating using rhodium ammine nitrite, ammonium hydroxide and hydrazine hydrate. The rhodium ammine nitrite was synthesized by reacting $K_3[Rh(NO_2)_3Cl_3]$ with $NH_4OH$ in this patent. For these two processes, the Rh reduction process is so fast that many bubbles are generated. Rh precipitation is also seen in the solution. These plating processes are impractical for coating a microchannel device due to bubble formation and Rh precipitation. Also the bubbles promote non-uniformity of the Rh coating. The Rh precipitation also results in a high cost because Rh is expensive.

JP58204168 (1983) provided a Rh plating bath using rhodium ammine chloride, a hydroxyl amine salt as a stabilizer and hydrazine as a reducing agent. The $Rh(NH_3)_6Cl_3$ was prepared by reacting $RhCl_3$ with concentrated $NH_4OH$ at 150° C. and 20 atm in a autoclave. However, the $Rh(NH_3)_6Cl_3$ is only slightly soluble in water and thus makes the plating process costly for handling so much waste liquid. Also many plating cycles are necessary to get the targeted loading for microchannel device due to the low volume/surface ratio. JP2000282248 (2000) reported Rh plating baths with ammonium-di(pyridine-2,6-dicarboxylate)-rhodium (III), $RhCl_x(NH_3)_{6-x}$ (x denotes 0 to 3), rhodium acetate, a triethylenetetramine complex of rhodium chloride or a diethylenetriamine complex of rhodium. The deposition is executed preferably at a pH 8 to 9 at 70-95° C. The above processes are very expensive and also bring challenges for applying Rh plating in microchannel devices. Additionally, most of the processes use chloride as Rh precursor. The presence of chloride in the plating bath leads to impure Rh plating. It is well known that chloride is a catalyst poison for many chemical reactions, e.g., steam methane reforming, combustion and partial oxidation.

Despite these and other efforts, there remains a need for improved methods of electrolessly depositing Rh.

Another aspect of the invention involves electrolessly plating platinum (Pt). Electroless plating of platinum has been known for many years. In U.S. Pat. No. 3,486,928 (1969), Rhoda and Vines used a solution containing $Na_2Pt(OH)_6$, NaOH, ethylamine and hydrazine for electroless Pt plating. However, hydrazine is not stable in this system and thus needs to be added in situ. In DE patent 2607988 (1977), JP patent 84-80764 (1984) and U.S. Pat. No. 6,391,477 (2002), $Pt(NH_3)_2(NO_2)_2$ was used as a Pt salt and hydrazine was a reducing agent for plating. But $Pt(NH_3)_2(NO_2)_2$ is hard to dissolve into water. Thus requiring numerous coating steps to get a catalyst high in Pt. In contrast, the present invention uses more soluble Pt salts enabling solutions containing 30 g Pt/L or more.

SUMMARY OF THE INVENTION

In a first aspect, this invention provides a method of electrolessly depositing Rh, comprising: forming an Rh-containing aqueous solution comprising a Rh amine complex having at least 1 g Rh/L (more preferably at least 3, and still more preferably at least 7 g Rh/L; and in some embodiments about 1 to about 10 g of dissolved Rh/L); wherein the Rh-containing aqueous solution is essentially free of chloride and nitrite; contacting a support with the Rh-containing aqueous solution; reacting the Rh-containing aqueous solution with a reducing agent; and depositing Rh onto the support. In some preferred embodiments, the solution is formed (or is capable of being formed) in pure water and/or at room temperature.

In another aspect, the invention provides a method of electrolessly depositing Rh using a plating bath using rhodium ammine hydroxide or rhodium ammine nitrate. Those salts do not contain chlorine so the plated Rh purity is high. It is found that rhodium ammine hydroxide has higher solubility than rhodium ammine chloride or rhodium ammine nitrate.

The methods of depositing Rh preferably comprise depositing at least 0.01 mg Rh per $in^2$ using a volume of aqueous solution of 100 ml or less. The temperature of the electroless deposition methods can be room temperature or above room temperature. More preferably, at least 0.1 mg Rh per $in^2$, and, in some embodiments, in the range of 0.1 to about 1 mg Rh per $in^2$. In some preferred embodiments of electrolessly forming Rh layers, the aqueous plating solution is formed by dissolving a solid compound having the stiochiometry $Rh(NH_3)_x(OH)_3$, where x is 3 to 6.

The invention also includes a method of electrolessly plating Pt, comprising: making a solution comprising Pt nitrate and Pt hydroxide, and applying the solution to a surface. In some preferred embodiments, the surface is a surface in a combustion channel (preferably a combustion microchannel).

In another aspect, the invention provides a method of selectively coating portions of a channel or channels in a microchannel device. Selected portions of a microchannel can be coated with a hydrophobic material (such as a wax) that acts as a mask preventing electroless deposition. The hydrophobic material can be subsequently burned out or removed with organic solvent. Alternatively, a heavy oil could be added to the channels and directed by gravity to fill selected regions or channels, the aqueous plating solution could not enter these regions and would plate out in the other regions. This selective coating approach could be used between coats, such as after a first metal (for example, Pt) layer is electrolessly deposited, a region of a microchannel or regions of microchannels can be selectively masked and then plated with a second metal (such as Rh) plated onto selected regions.

The invention also includes catalysts made by using of the methods described. In many preferred embodiments, catalysts are formed inside microchannels; however, other applications are also envisioned, for example, for the addition of catalyst metal(s) to catalyst in a packed bed.

In a further aspect, the invention provides a method of electrolessly depositing Rh, comprising: contacting a support with a solution comprising Rh and at least one promoter cation selected from the group consisting of copper cation and lead cation; reacting the Rh-containing aqueous solution with a reducing agent; and depositing Rh onto the support. This method enhanced plating rate in open vessels; however, no rate enhancement from this technique was observed in microchannels.

In a further aspect, the invention provides microchannel apparatus, comprising: a flow path comprising a microchannel; an electrolessly-applied passivation coating on at least one wall defining the flow path; and a catalyst in the microchannel. The catalyst and the electrolessly-applied passivation coating have different compositions; and the electrolessly-applied passivation coating comprises at least one element selected from the group consisting of: Pt, Cu, Au, Ag, Pd, Rh, Ru, Re, Zn, and combinations thereof. Preferably, the passivation coating is metallic. These metals will cover the potential cooking sites (e.g., acid sites and Ni, Fe, Co, Cr sites) at the surface of the heat-treated alloys, thus suppressing cooking. Without coke formation, carburization would also be suppressed. These metals could be electrolessly plated on the heat-treated Ni-aluminide or Pt-aluminide surface. The plating thickness could be controlled by controlling plating conditions, such as concentration, temperature and plating time. Additionally Pt, Au and Cu are good catalysts for water gas shift reactions. They could effectively convert CO and steam to $CO_2$ and $H_2$. Lowering CO concentration in the SMR product channel is expected to further decrease coke formation from CO.

In another aspect, the invention provides a method of conducting a steam reforming reaction in a microchannel reactor, comprising: passing a process steam through a first section of a microchannel; wherein the first section comprises an electrolessly-applied coating comprising Pt, Au, or Cu; wherein the process stream comprises CO and $H_2O$ (note that the CO could be formed in situ by partial oxidation) and further wherein the CO and $H_2O$ in the first section reacts over the electrolessly-applied coating to form $CO_2$; and passing gas from the first section into a second section, wherein the second section comprises a high temperature steam reforming catalyst, and conducting a steam reforming reaction in the second section.

In a further aspect, the invention provides a method of making a catalyst, comprising: electrolessly depositing a catalyst metal on a support; and conducting at least one cycle of oxidation and reduction to form a catalyst comprising a reduced metal on a support. As shown in the Examples section, this method was unexpectedly found to produce a catalyst having superior properties. In the oxidation cycle, the catalyst is exposed to a gas in which there is at least one gas containing oxidizing compounds, e.g., air, $O_2$ and $N_2O$. The reducing atmosphere is a gas mixture containing $H_2$, CO, hydrocarbon or other reducing agent(s). In an oxidizing atmosphere, the metal (Pt in some preferred embodiments) may be partially or completely oxidized to form oxides or an mixture of metal and oxides. In a reducing atmosphere, the Pt oxides may be reduced back to metallic Pt. After several redox processes, the active catalyst distribution and the particle morphology may change. Consequently, the catalyst performance may be improved by this redox treatment. Other conditioning procedures could use liquid or solution reagents such as acids, bases, etching solutions, chelating agents, or any of a variety of agents known to those skilled in the art. CVD processes could also be employed to introduce additional elements or to modify the surface morphology. This activation process can also be applied to any other electrolessly plated catalysts, such as Rh, Pd, Ag, Au, Cu, Ni, Fe, Co, etc, or combinations or subcombinations of these, but not limited to these. The electroless plated metals can be in combination with any of a wide range of promoter or stabilizer elements, many of which are well known to those skilled in the art. Oxidation and reduction are preferably carried out at a temperature of at least 500° C., more preferably at least 700° C., and in some embodiments in the range of 750 to 1000° C. In some preferred embodiments, there are at least 3 oxidation/reduction cycles. In the examples, the catalyst was Pt on an alumina surface (the alumina was thermally grown from an aluminide).

In a further aspect, the invention provides a method of electrolessly depositing Pt, comprising: forming an Pt-containing aqueous solution comprising, or formed from, $Pt(NH_3)_4(NO_3)_2$, $Pt(NH_3)_4(OH)_2$, or $Pt(NH_3)_2(OH)_2$; contacting a support with the Pt-containing aqueous solution; reacting the Pt-containing aqueous solution with a reducing agent; and depositing Pt onto the support. The invention also includes the catalyst prepared by this method. In some embodiments, the catalyst comprises a Pt layer on alumina wherein the Pt layer consists essentially of Pt crystallites in the size range of 0.2 to 1.5 micrometers, where "size" is the maximum dimension of a particle.

In another aspect, the invention provides a method of combusting a hydrocarbon, comprising: passing a process stream comprising a hydrocarbon and oxygen through a flow path at a temperature of at least 750° C. and a contact time of 10 ms or less; wherein the flow path is defined by channel walls; wherein at least one of the channel walls comprises a wall catalyst coating; wherein the wall catalyst coating comprises at least 3 mg/in$^2$ Rh and at least 3 mg/in$^2$ Pt and more than 10 mg/in$^2$ (Pt+Rh); and converting at least 80% of the oxygen and at least 10% of the hydrocarbon in the process stream and forming CO and water. Preferably, the catalyst maintains essentially constant activity over at least 500 hours of operation without regeneration. Surprisingly, it was found that a catalyst having lower loading deactivated, while the higher loading catalyst did not deactivate. In some embodiments, the zirconia has a loading in the range of 2 to 20 mg/in$^2$. In some embodiments, the wall catalyst coating comprises at least 5 mg/in$^2$ Rh and at least 5 mg/in$^2$ Pt and more than 15 mg/in$^2$ (Pt+Rh).

In another aspect, the invention provides a catalyst comprising Pt electrolessly deposited on zirconia. The invention also provides a method of making a catalyst in which Pt is electrolessly deposited on a support comprising zirconia (Ce stabilized zirconia could also be used). Pt—ZrO$_2$ and Pt—CeO$_2$—ZrO$_2$ powder catalysts for SMR are described in K. Kusakabe, K. I. Sotowa, T. Eda, Y. Iwamoto, Fuel Process. Tech., 86 (2004) 319, and J. Wei, E. Iglesia, J. Phys. Chem. B, 108 (2004) 4094. In these publications, the catalysts were synthesized by incipient wetness impregnation.

The invention also provides a catalyst comprising Pt disposed on zirconia and further characterizable by an active stability such that, if tested at a temperature of 880° C. (the high temperature at the surface of the catalyst) and exposed to a process stream made of steam and methane at a 3:1 ratio, 27 atm, and a contact time of 4.2 ms for about 165 hours without regeneration, methane conversion is about 75%. The test should be conducted in the type of microchannel reactor described in the examples, or one of similar construction. In some embodiments, the catalyst comprises a coating that comprises at least 3 mg/in$^2$ Pt, more preferably at least 5 mg/in$^2$ Pt.

In still another aspect, the invention provides a method of methane steam reforming, comprising: passing steam and methane in contact with a catalyst comprising Pt disposed on zirconia for at least 165 continuous hours without regeneration, at a temperature of about 850 to 900° C., a contact time of 15 ms or less, and obtaining a methane conversion, after at least 165 hours, of at least 70%. More preferably, methane conversion is at least about 75%. In some preferred embodiments, contact time is 10 ms or less, in some embodiments, 5 ms or less, and in some embodiments in the range of 10 to about 4 ms.

The inventive methods can be used to form metal coatings in complex microchannels, for example, by adding an electroless plating composition into a complex microchannel, and depositing metal from the solution onto an internal surface of the complex microchannel. The invention also provides methods to selectively coat a portion or portions of a microchannel. The inventive methods can be used for refurbishing a spent catalyst (i.e., a catalyst that had been used at elevated temperature and that suffered at least a 10% (preferably at least 20%) loss in catalytic activity.

The invention also provides methods of conducting reactions or other chemical processes. For example, combustion over an electrolessly-applied plating of Pt and Rh. For another example, the invention provides a two zone combustion process, comprising: combusting a fuel-rich composition in a first zone of a reaction channel, wherein the first zone comprises Pt and Rh coated onto a reaction channel wall; and combusting a fuel-lean composition in a second zone of the reaction channel, wherein the second zone comprises Pt coated onto a reaction channel wall. In the inventive methods, the catalyst can be additionally characterized by the method by which the catalyst was made or the measurable reactivity properties of the catalyst, apparatus, or system.

Inventive methods can be used to electrolessly plate on any substrate, including powders (oxides, catalyst supports, zeolites, etc.), glass, fibers, ceramic materials and metallic materials. The substrates could have a flat surface or a modified surface with various geometries (e.g., pores and microchannels). The surface of the substrates may be treated with other metals prior to Rh plating; for example plating with Cu, Pt or Pd, prior to Rh plating. This process can also be used for plating alloys (e.g., Pt—Rh alloy) simultaneously. The substrate surface may also be modified with pre-coating rare earth oxide, alkaline earth oxide and transition metal oxides prior to electroless plating.

Electroless plating on substrates could be used for catalysts, electronics, optics, fuel cells, electrical contacts, gas sensors, corrosion protection, insoluble electrodes, gas turbine engines, X-ray mirrors, jewelry, medical implants and many other applications.

The present invention also provides microchannel apparatus comprising electrolessly plated coatings, systems and methods of conducting reactions through microchannel devices with coated microchannels. The invention also includes the optional coating of pipes, tubes, or other structures attached to microchannel apparatus.

In a preferred embodiment, the invention provides a method of steam reforming or combustion over an electrolessly-applied plating comprising Rh, or comprising Pt and Rh. Other preferred methods that can be conducted over the catalysts described herein include partial oxidation, autothermal reforming, and CO$_2$ reforming.

The inventive methods offer numerous advantages. For example, the methods may be used to provide a uniform coating even in complex channel geometries, and electroless coating won't occlude jet holes.

Systems of the invention can be described as including apparatus and/or catalyst in combination with reactants and/or products. Optionally, systems can be further characterized by the conditions at which they operate.

In various embodiments, the invention can provide advantages including the following: easy operation (the plating can be performed from room temperature to high temperatures and on any substrates, including powders (oxides, catalyst supports, etc.), glass, ceramics, fibers and metals; the ability to provide a uniform coating even in complex channel geometries; providing a coating that doesn't occlude small orifices within microchannels; low cost (the plating process is simple because only Rh salt and reducing agent are used); all dissolved Rh can be plated onto a substrate with no Rh precipitation; less waste solution (only a small amount of ammonium hydroxide is generated in the used bath); plated surface is not contaminated with chloride (previously disclosed recipes use rhodium chloride as precursor); lower rate of bubble formation which means a more uniform coating when done in-situ in a microchannel reactor; and ability to plate with other metal (e.g., Pt) in the same bath simultaneously.

GLOSSARY OF TERMS USED

"Metal aluminide" refers to a metallic material containing 10% or more Metal and 5%, more preferably 10%, or greater Aluminum (Al) with the sum of Metal and Al being 50% or more. These percentages refer to mass percents. Preferably, a metal aluminide contains 50% or more Metal and 10% or greater Al with the sum of Ni and Al being 80% or more. In embodiments in which Metal and Al have undergone significant thermal diffusion, it is expected that the composition of a Metal-Al layer will vary gradually as a function of thickness so that there may not be a distinct line separating the Metal-Al layer from an underlying Metal-containing alloy substrate. The term "aluminide" is used synonamously with metal aluminide.

A preferred metal aluminide is nickel aluminide (NiAl). "Nickel aluminide" refers to a material containing 10% or more Ni and 10% or greater Al with the sum of Ni and Al being 50% or more. These percentages refer to mass percents. Preferably, a nickel aluminide contains 20% or more Ni and 10% or greater Al with the sum of Ni and Al being 80% or more. In embodiments in which Ni and Al have undergone significant thermal diffusion, it is expected that the composition of a Ni—Al layer will vary gradually as a function of thickness so that there may not be a distinct line separating the Ni—Al layer from an underlying Ni-based alloy substrate.

A "catalyst material" is a material that catalyzes a desired reaction. It is not alumina. A catalyst material "disposed over" a layer can be a physically separate layer (such as a sol-deposited layer) or a catalyst material disposed within a porous, catalyst support layer. "Disposed onto" or "disposed over" mean directly on or indirectly on with intervening layers. In some preferred embodiments, the catalyst material is directly on a thermally-grown alumina layer.

A "catalyst metal" is the preferred form of catalyst material and is a material in metallic form that catalyzes a desired reaction. Particularly preferred catalyst metals are Pd, Rh and Pt.

A "chemical unit operation" comprises reactions, separations, heating, cooling, vaporization, condensation, and mixing.

As is conventional patent terminology, "comprising" means including and when this term is used the invention can, in some narrower preferred embodiments, be described as "consisting essentially of" or in the narrowest embodiments as "consisting of" Aspects of the invention described as "comprising a" are not intended to be limited to a single component, but may contain additional components. Compositions "consisting essentially of" a set of components allow other components that so not substantially affect the character of the invention, and, similarly, compositions that are "essentially" without a specified element do not contain amounts of the element as would substantially affect the desired properties.

Unless stated otherwise, "conversion percent" refers to absolute conversion percent throughout these descriptions. "Contact time" is defined as the total catalyst chamber volume (including the catalyst substrate volume) divided by the total volumetric inlet flowrate of reactants at standard temperature and pressure (STP: 273K and 1.013 bar absolute). Catalyst chamber volume includes any volume between a catalyst coating (or other flow-by catalyst arrangement) and the opposite wall of a reaction channel.

A "complex microchannel" is an apparatus that includes one or more of the following characteristics: at least one contiguous microchannel has a turn of at least 45°, in some embodiments at least 90°, in some embodiments a u-bend; a length of 50 cm or more, or a length of 20 cm or more along with a dimension of 2 mm or less, and in some embodiments a length of 50-500 cm; at least 2 adjacent channels, having an adjacent length of at least one cm that are connected by plural orifices along a common microchannel wall where the area of orifices amounts to 20% or less of the area of the microchannel wall in which the orifices are located and where each orifice is 0.6 mm$^2$ or smaller, in some embodiments 0.1 mm$^2$ or smaller—this is a particularly challenging configuration because a coating should be applied without clogging the holes; or at least two, in some embodiments at least 5, parallel microchannels having a length of at least 1 cm, have openings to an integral manifold, where the manifold includes at least one dimension that is no more than three times the minimum dimension of the parallel microchannels (for example, if one of the parallel microchannels had a height of 1 mm (as the smallest dimension in the set of parallel microchannels), then the manifold would possess a height of no more than 3 mm). An integral manifold is part of the assembled device and is not a connecting tube. A complex microchannel is one type of interior microchannel.

In preferred embodiments, an electroless coating is contiguous over at least 1 cm, more preferably at least 5 cm, of a microchannel.

The phrase a "coating grows away from the wall" refers to the direction that a coating grows—either by thermal oxidation or an accretion process such as electroless plating.

A "contiguous microchannel" is a microchannel enclosed by a microchannel wall or walls without substantial breaks or openings—meaning that openings (if present) amount to no more than 20% (in some embodiments no more than 5%, and in some embodiments without any openings) of the area of the microchannel wall or walls on which the opening(s) are present.

"Directly disposed" means that a material is directly applied to a specified layer. There is not an intervening washcoating, nor is the material codeposited with a washcoated catalyst support. "Directly deposited" has the same meaning. An electrolessly applied layer can be directly deposited electrolessly on any of the substrates mentioned herein.

An "interior microchannel" is a microchannel within a device that is surrounded on all sides by a microchannel wall or walls except for inlets and outlets, and, optionally, connecting holes along the length of a microchannel such as a porous partition or orifices such as connecting orifices between a fuel channel and an oxidant channel. Since it is surrounded by walls, it is not accessible by conventional lithography, conventional physical vapor deposition, or other surface techniques.

An "insert" is a component that can be inserted into a channel.

A "manifold" is a header or footer that connects plural microchannels and is integral with the apparatus.

Measurement techniques—For all coatings, "average thickness" can be measured by cross-sectional microscopy (obtained by cutting open a microchannel device) or, for coatings that are about 5 µm thick or less, by EDS elemental analysis. In the case of channels connected to a common manifold or otherwise connected to be filled from the same inlet, the "average thickness" is averaged over all the channels, or for a large number of connected channels, at least 10 channels selected to fairly represent the totality of the connected channels. Measurements should be made over the entire length of a contiguous coating; that is, not just for 1 cm selected out of a larger contiguous coating. "Coating loading" is measured the same as average thickness except that height and/or thickness (or elemental analysis) of the coating is measured to get a volume or mass. Unless specified as a corner measurment, average coating thickness should be measured along the center line between corners (if present), and any set of corners can be selected. Corner thickness can be measured on a single corner; however, the corner must be representative (not an aberration).

A "microchannel" is a channel having at least one internal dimension (wall-to-wall, not counting catalyst) of 1 cm or less, preferably 2 mm or less (in some embodiments about 1.0 mm or less) and greater than 100 nm (preferably greater than 1 μm), and in some embodiments 50 to 500 μm. Microchannels are also defined by the presence of at least one inlet that is distinct from at least one outlet. Microchannels are not merely channels through zeolites or mesoporous materials. The length of a microchannel corresponds to the direction of flow through the microchannel. Microchannel height and width are substantially perpendicular to the direction of flow of through the channel. In the case of a laminated device where a microchannel has two major surfaces (for example, surfaces formed by stacked and bonded sheets), the height is the distance from major surface to major surface and width is perpendicular to height.

"Ni-based" alloys are those alloys comprising at least 30%, preferably at least 45% Ni, more preferably at least 60% (by mass). In some preferred embodiments, these alloys also contain at least 5%, preferably at least 10% Cr.

A "post-assembly" coating is applied onto three dimensional microchannel apparatus. This is either after a laminating step in a multilayer device made by laminating sheets or after manufacture of a manufactured multi-level apparatus such as an apparatus in which microchannels are drilled into a block. This "post-assembly" coating can be contrasted with apparatus made by processes in which sheets are coated and then assembled and bonded or apparatus made by coating a sheet and then expanding the sheet to make a three-dimensional structure. For example, a coated sheet that is then expanded may have uncoated slit edges. The post-assembly coating provides advantages such as crack-filling and ease of manufacture. Additionally, the aluminide or other coating could interfere with diffusion bonding of a stack of coated sheets and result in an inferior bond since aluminide is not an ideal material for bonding a laminated device and may not satisfy mechanical requirements at high temperature. Whether an apparatus is made by a post-assembly coating is detectable by observable characteristics such as gap-filling, crack-filling, elemental analysis (for example, elemental composition of sheet surfaces versus bonded areas) Typically, these characterisitics are observed by optical microscopy, electron microscopy or electron microscopy in conjunction with elemental analysis. Thus, for a given apparatus, there is a difference between pre-assembled and post-assembled coated devices, and an analysis using well-known analytical techniques can establish whether a coating was applied before or after assembly (or manufacture in the case of drilled microchannels) of the microchannel device. In preferred embodiments, an electroless plating is applied post-assembly.

"Unit operation" means chemical reaction, vaporization, compression, chemical separation, distillation, condensation, mixing, heating, or cooling. A "unit operation" does not mean merely fluid transport, although transport frequently occurs along with unit operations. In some preferred embodiments, a unit operation is not merely mixing.

DESCRIPTION OF THE INVENTION

Electroless Plating

Figure 1:
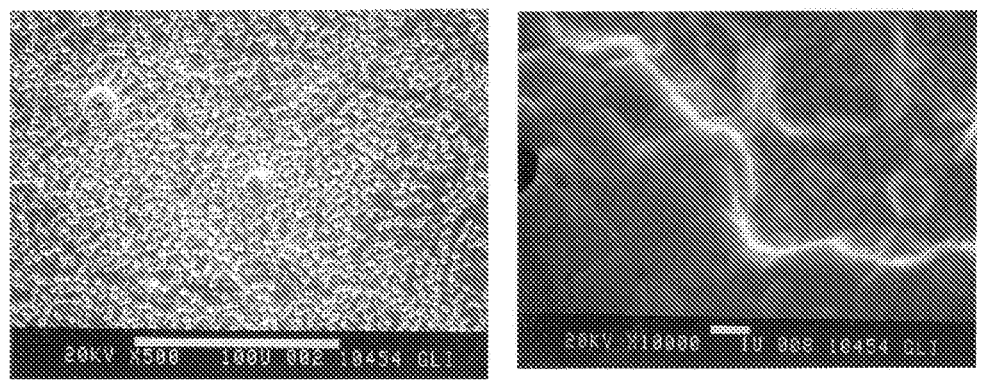
FIG. 1 shows SEM micrographs of a heat-treated aluminized alloy 617 coupon with 28 mg/in$^2$ Pt plating

An electroless plating solution comprises a metal compound and a reducing chemical. A complexing agent may be added to prevent reduction of the metal ions in solution. In some embodiments, the reduction process may be catalyzed by a small amount of catalytic metal ions. Preferred metals for the electroless deposition include Cu, Ni, Fe, Co, Au, Ag, Pd, Pt, Sn, Ir, Rh and combinations thereof. After plating, the residual solution could be drained out.

We discovered that metal ions such as Cu generally speed plating of metals (such as Rh) in relatively large volumes but were not found to speed coating in microchannels. Also, we unexpectedly discovered that, in microchannels, the electroless plating rate could be increased by about an order of magnitude by recirculating the plating solution through the microchannel.

The use of electroless plating of catalytic metals on reactor walls, both conductive and non-conductive, can be used to create a uniform metal coating inside a channel. Such an electroless plating solution could comprise a water soluble metal salt, a reducing agent such as hydrazine hydrate, possibly a stabilizer such as EDTA to prevent precipitation of the plating metal, optionally an accelerator such as 3,4-dimethoxybenzoic acid or an acid such as acetic acid to adjust the pH for optimum plating. For a microchannel reactor the electroless plating solution is preferably filled (to the desired height) within the channels prior to the initiation of the reaction. The solution could be introduced at room temperature or below and then heated to the requisite plating temperature. In some applications it may be important that the plating process end before the plating solution is drained, particularly if the draining process is long relative to the plating process, to achieve a uniform coating. This can be accomplished by, for example, controlling a plating composition/reaction in which one of the essential reactants is depleted before the draining process begins. Another approach would be to reduce the plating temperature prior to draining. For example, in addition to the draining issues, the plating liquid should be selected to be stable in microchannels so that particles will not form in solution and drift by gravity.

Pt can be electrolessly deposited. In this method, the plating bath includes a Pt compound and a reducing agent. A complexing agent may also be added if necessary. The plating bath may have 0.001 g to 200 g Pt per liter, preferably 0.01 g to 100 g Pt per liter. Examples of Pt compounds include $Pt(NH_3)_4(NO_3)_2$, $Pt(NH_3)_4(OH)_2$, $PtCl_2(NH_3)_2$, $Pt(NH_3)_2(OH)_2$, $(NH_4)_2PtCl_6$, $(NH_4)_2PtCl_4$, $Pt(NH_3)_2Cl_4$, $H_2PtCl_6$, and $PtCl_2$. $Pt(NH_3)_4(NO_3)_2$ and $Pt(NH_3)_4(OH)_2$ are especially preferred and lead to unexpected results. The reducing agents may include hydrazine derivatives (such as hydrazine hydrate), and boron hydrides (such as $NaBH_4$). Their concentration could be from 0.001 g to 800 g per liter, preferably 0.01 g to 100 g per liter. The complexing agents could be, for example, hydroxylamine chloride, hydrazine dichloride, ammonium hydroxide and/or EDTA. Their concentration could be from 0.001 g to 200 g per liter, preferably 0.01 g to 100 g per liter.

The pH in the solution could be adjusted by acids or ammonium and alkali hydroxides. The pH could be 4-14, more preferably, 6-14. The plating process is conducted from 1-90° C., preferably from room temperature to 80° C.

The invention includes methods of forming electrolessly plated Pt. In this method, platinum amine nitrate and platinum amine hydroxide ($Pt(NH_3)_4(OH)_2$) are combined and Pt deposits onto a surface. Preferably this is conducted at room temperature. It has been surprisingly discovered that this method can occur in conjunction with an induction time (typically about 1 to 2 hour), this allows portions of channels to be filled with plating solution without plating other portions of the channel.

In some preferred embodiments of the invention, a metal or metals are deposited directly onto an alumina layer, in some cases a dense alumina layer. In some embodiments, an electroless plating is deposited directly over an old catalyst (thus refurbishing a spent catalyst).

For enhanced stability to high temperature fuel rich combustion, an electrolessly-plated Pt layer is preferably combined with Rh. One method by which this can be done is by applying a layer of Rh over a Pt layer. Preferred Rh sources are rhodium amine compounds, preferably $Rh(NH_3)_x(OH)_y$, in which the sum of x and y is six. The Rh layer can be electrolessly deposited by known methods that can include the addition of ammonium hydroxide to control pH.

It has been discovered that a combination of catalysts is desired for a combustion channel—in the inventive combination, there are at least two zones in a combustion channel; in one zone (operated under fuel rich conditions) there is electrolessly deposited Pt and Rh; while a second zone (to be operated under fuel lean conditions), includes Pt (preferably electrolessly deposited) or Pd (preferably electrolessly deposited) or Pt and Re (which could be slurry coated) or Pd and Pt (preferably both are electrolessly deposited). The electrolessly deposited Pd has been found to exhibit excellent conversion of hydrogen and CO, and a highly stable methane conversion (at least 42 hours at 850° C., at essentially constant conversion).

Electrolessly plated Pt, or electrolessly plated Pd, or electrolessly plated Pt—Rh can be used as a catalyst for steam reforming of hydrocarbons (preferably methane). An electrolessly plated Pt—Rh catalyst has been found to be stable and exhibit excellent adhesion.

The invention also provides a novel method of forming electrolessly plated Rh. In this method, a chlorine-free and nitrite ($NO_2$)-free Rh ammine complex is reacted with a reducing agent and Rh deposits onto a surface. Preferably this is conducted at room temperature. It has been discovered that Rh(amine)(hydroxide or nitrate ($NO_3$)) (which could be termed $Rh(NH_3)_xY_z$ where Y=hydroxide and/or nitrate, x=3 to 6, y=2 to 4) have surprisingly high solubility in aqueous plating solutions. The use of solutions of these complexes enables chloride- and nitrite-free superior coatings with only one, or relatively few coats.

In some preferred embodiments of the invention, Rh is deposited directly onto an alumina layer, in some cases a dense alumina layer. In some embodiments, an electroless Rh plating is deposited directly over an old catalyst (thus refurbishing a spent catalyst). Rhodium ammine nitrate can be prepared from the reaction between rhodium nitrate and ammonium hydroxide. Rhodium ammine hydroxide can be prepared from anion exchange using ion-exchange resin and rhodium ammine nitrate or rhodium ammine chloride. The rhodium ammine hydroxide can also be prepared from reaction between rhodium ammine chloride and silver hydroxide or oxide. Rhodium ammine chloride can be purchased or prepared from the reaction of rhodium chloride and ammonium hydroxide.

Other compounds that can be used as a Rh source, include: rhodium ammine hydroxide, rhodium ammine nitrate, rhodium ammine acetate, rhodium ammine sulfate, rhodium ammine sulfite, rhodium ammine bromide and rhodium ammine iodide.

To plate Rh, the rhodium ammine hydroxide or rhodium ammine nitrate is reacted with a reducing agent. Reducing agents include: hydrazine (preferred), sodium hypophosphite, dimethyl amine borane, diethyl amine borane and sodium borohydride, preferably hydrazine. In the plating bath, stabilizers or complexing agents, such as ammonium hydroxide, hydroxylamine salt and hydrazine dichloride, may also be added, but are not necessary. The plating could be performed at room temperature or high temperature, in acidic solution or basic solution. Although not critical to the present invention, the reaction between rhodium ammine hydroxide and hydrazine may be written:

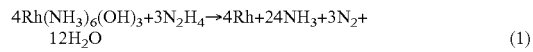

$$4Rh(NH_3)_6(OH)_3 + 3N_2H_4 \rightarrow 4Rh + 24NH_3 + 3N_2 + 12H_2O \quad (1)$$

Only ammonium hydroxide is left in the used plating bath.

The Rh layer can be essentially pure Rh, or may contain additional elements such as Pt or Pd. Electrolessly plated Rh, or electrolessly plated Pd, or electrolessly plated Pt—Rh can be used as a catalyst for steam reforming of hydrocarbons (preferably methane), carbon dioxide reforming, partial oxidation, and auto-thermal reforming of hydrocarbons.

Coatings

For flat or substantially flat substrates (such as a flat microchannel wall), a coating can be characterized by the amount of desired material on a geometric surface area; that is, an area that can be measured with a ruler. For purposes of the present invention, a microchannel wall with embedded surface features is considered a substantially flat surface. For coatings in a rectangular channel, the surface area would be the sum of the surface areas of the four walls (again, the geometric surface area, not the surface area measured by BET). In some preferred embodiments, the catalyst contains at least 0.3 mg/cm² catalytic material (for example, Rh), in some preferred embodiments at least 0.6 mg/cm² catalytic material, and in some embodiments 0.2 to 2 mg/cm² catalytic material.

Unless otherwise specified, elemental analyses of wall coatings should be determined using energy dispersive X-ray spectroscopy (EDS) at 20 kV excitation energy (at 100×, or if 100× is larger than the area available, then the largest available area for SEM, recognizing that some modifications may be required if such measurment conditions are impracticable for particular systems). As is well-known, this technique measures the surface composition, as well as some thickness below the surface.

Some catalysts of this invention have a surface area, as measured by $N_2$ adsorption BET, of 10 m²/g or less, and in some embodiments a surface area of 5 m²/g or less.

An electroless catalyst coating can be applied to any support. One preferred support material is alumina. An "alumina support" contains aluminum atoms bonded to oxygen atoms, and additional elements can be present. An alumina support may include a stabilizing element or elements that improve the stability of the catalyst in conditions accompanying the high temperature combustion of hydrocarbons. Stabilizing elements typically are large, highly charged cations. In preferred embodiments, the alumina support is stabilized by La. In this invention, a "stabilized alumina support" is an alumina support containing at least one stabilizing element. A preferred stabilized alumina support contains 1 to 10, more preferably 3 to 7 weight percent of a stabilizing element or elements (preferably La).

A combustion catalyst preferably contains Pt. The platinum content in a catalyst can be described either in terms of weight percent or in terms of mass per geometric surface area of substrate. Weight percent is based on the weight of platinum as a percent of catalyst powder, catalyst pellets, or washcoat; it does not include the weight of an underlying substrate and does not include the weight of interlayers between a washcoat (or washcoats) and an underlying substrate. For example, in the case of an alloy felt washcoated with alumina and Pt, the weight % would be $Pt/(Pt+Al_2O_3)\times 100\%$. For a metal coupon that has been aluminized, then oxidized, then treated with solution of alumina and lanthanum and Pt, the weight of the oxidized aluminized layer would not be included in the calculation of weight % Pt. In other preferred embodiments, the catalyst contains at least 3.0 mg/in$^2$ Pt, more preferably 4.5 mg/in$^2$ Pt (15 mg/in$^2$ of a 30 wt % Pt on alumina washcoat), in some preferred embodiments at least 6 mg/in$^2$ Pt, and in some embodiments 6 to 12 mg/in$^2$ Pt. For purposes of this measurement, the area refers to the geometrical area of the substrate; for a flat surface such as a foil or coupon, this area is quite simple, for a honeycomb or finned substrate or reaction channel, it would include all the surfaces that are coated by catalyst. The amount of Pt or the weight percent of Pt can be determined by known methods of chemical analysis.

In some preferred embodiments, the catalyst comprises a metal, ceramic or composite substrate, including insertable substrates, and includes a layer or layers of a catalyst metal or metals electrolessly deposited thereon. Preferably, the substrate is thermally conductive. A preferred substrate is a finned substrate that is characterized by the presence of fins (such as square-wave type fins) on the substrate's surface. These fins may, for example, take the form of fins etched in the wall of an integrated reactor or a finned insert (such as a flat metal plate with one grooved surface) that can be inserted into a combustion chamber of a microreactor. In some cases, the reactor can be refurbished by replacing an insert. One method of fabrication within a microchannel comprises the use of a slitting saw, partial etching using a photochemical process, or a laser EDM. This type of support provides numerous advantages including: high heat flux with short heat transfer distances, high surface area, and low pressure drop. Preferably, the support has a height (including fins) of less than 5 mm and preferably less than 2 mm and a fin-to-fin separation of 1000 µm or less, and in some embodiments, a fin-to-fin separation of 150 to 500 µm. Alternatively, the catalyst may take any conventional form such as a powder or pellet.

In some embodiments, a catalyst is disposed directly on a dense alumina layer. In some other embodiments, the catalyst includes an underlying large pore substrate. Examples of preferred large pore substrates include commercially available metal foams and metal felts. Prior to depositing any coatings, a "large pore substrate" has a porosity of at least 5%, more preferably 30 to 99%, and still more preferably 70 to 98%. In some preferred embodiments, a large pore substrate has a volumetric average pore size, as measured by BET, of 0.1 µm or greater, more preferably between 1 and 500 µm. Preferred forms of porous substrates include foams and felts and these are preferably made of a thermally stable and conductive material, preferably a metal such as stainless steel or FeCrAlY alloy. These porous substrates can be thin, such as between 0.1 and 1 mm. Foams are continuous structures with continuous walls defining pores throughout the structure. Felts are nonwoven fibers with interstitial spaces between fibers and include tangled strands like steel wool. Felts are conventionally defined as being made of nonwoven fibers. In one embodiment, the large-pore substrate has a corrugated shape that could be placed in a reaction chamber (preferably a small channel) of a steam reformer. Various substrates and substrate configurations are described in U.S. Pat. No. 6,680,044 which is incorporated by reference.

In some embodiments, a catalyst's properties (such as stability, conversion and selectivity) are defined by the following test procedure (referred to as "Test Procedure 1") and is based on the reactions described in the Examples in the section entitled "Microchannel Insert Testing". Catalysts should be tested as (or on) an insert in the test reactor. Reactors and systems can be characterized by adjusting the flow rates to obtain the same contact times as in the run plans. In this test procedure (which can be further understood with reference to the Examples), the catalyst can be coated on to a FeCrAlY or aluminized alloy 617 substrate which is inserted into a single microchannel test reactor with a 10 mil gap for the reactant gases. Combustion catalysts can be tested in a wide range of simulated gas compositions, representative of fuel rich conditions existing in various zones of a microchannel reactor in which air is added in stages to the combustion fuel.

In addition to electroless platings, catalysts can be applied using techniques that are known in the art. These additional catalytic and promoter elements can be chosen for their impact on the performance of the catalytic reaction, for their impact on the microstructure and adhesion of the catalyst to the support, or both. These added elements can be chosen from the alkali, alkaline earth, transition metals, rare earth elements, or some combination of these elements. The elements can be chosen based on their ability to improve performance, stability, adhesion, or some combination of these properties in standard experimental tests. Impregnation with aqueous salts is preferred. Pt, Rh, and/or Pd are preferred in some embodiments. Typically this is followed by heat treatment and activation steps as are known in the art. Salts which form solutions of pH>0 are preferred.

The Rh content in a catalyst or other article can also be described either in terms of weight percent or in terms of mass per geometric surface area of substrate. Weight percent is based on the weight of rhodium (and/or Rh and Pt) as a percent of catalyst powder, catalyst pellets, or washcoat; it does not include the weight of an underlying substrate and does not include the weight of interlayers between a washcoat (or washcoats) and an underlying substrate. In some preferred embodiments the coated article contains at least 0.01 mg/in$^2$ Rh, and in some embodiments 0.1 to 100 mg/in$^2$ Rh.

Microchannel Apparatus

Microchannel apparatus is characterized by the presence of at least one channel having at least one dimension (wall-to-wall, not counting catalyst) of 1.0 cm or less, preferably 2.0 mm or less (in some embodiments about 1.0 mm or less) and greater than 100 nm (preferably greater than 1 µm), and in some embodiments 50 to 500 µm. Both height and width are substantially perpendicular to the direction of flow of reactants through the reactor. Microchannels are also defined by the presence of at least one inlet that is distinct from at least one outlet—microchannels are not merely channels through zeolites or mesoporous materials. The height and/or width of a microchannel is preferably about 2 mm or less, and more preferably 1 mm or less. The length of a microchannel is typically longer. Preferably, the length of a microchannel is greater than 1 cm, in some embodiments greater than 20 cm, in some embodiments greater than 50 cm, and in some embodiments in the range of 1 to 100 cm. The sides of a microchannel are defined by microchannel walls. These walls are preferably made of a hard material such as a ceramic, an iron based alloy such as steel, or a Ni-, Co- or Fe-based superalloy such as monel. The choice of material for the walls of the reaction channel may depend on the conditions for which the apparatus is designed to operate. In some embodiments, the reaction chamber walls are comprised of a stainless steel or Inconel® which is durable and has good thermal conductivity. The alloys should be low in sulfur, and in some embodiments are subjected to a desulfurization treatment prior to formation of an aluminide. Typically, channel walls are comprised of the material that provides the primary structural support for the microchannel apparatus. The microchannel apparatus can be made by known methods (except for the coatings and treatments described herein), and in some preferred embodiments are made by laminating interleaved plates (also known as "shims"), and preferably where shims designed for reaction channels are interleaved with shims designed for heat exchange. Of course, as is conventionally known, "reactors' do not include jet engine parts. In preferred embodiments, microchannel apparatus does not include jet engine parts. Some microchannel apparatus includes at least 10 layers laminated in a device, where each of these layers contain at least 10 channels; the device may contain other layers with less channels.

Microchannel reactors preferably include a plurality of microchannel reaction channels. The plurality of microchannel reaction channels may contain, for example, 2, 10, 100, 1000 or more channels. In preferred embodiments, the microchannels are arranged in parallel arrays of planar microchannels (an array comprises plural, parallel channels), for example, at least 3 arrays of planar microchannels. In some preferred embodiments, multiple microchannel inlets are connected to a common header and/or multiple microchannel outlets are connected to a common footer. During operation, the heat exchange microchannels (if present) contain flowing heating and/or cooling fluids. Non-limiting examples of this type of known reactor usable in the present invention include those of the microcomponent sheet architecture variety (for example, a laminate with microchannels) exemplified in U.S. Pat. Nos. 6,200,536 and 6,219,973 (both of which are hereby incorporated by reference). In some embodiments, the reaction microchannel (or microchannels) contains a bulk flow path. The term "bulk flow path" refers to an open path (contiguous bulk flow region) within the reaction chamber. A contiguous bulk flow region allows rapid fluid flow through the reaction chamber without large pressure drops. In some preferred embodiments there is laminar flow in the bulk flow region. Bulk flow regions within each reaction channel preferably have a cross-sectional area of $5\times10^{-8}$ to $1\times10^{-2}$ m$^2$, more preferably $5\times10^{-7}$ to $1\times10^{-4}$ m$^2$. The bulk flow regions preferably comprise at least 5%, more preferably at least 50% and in some embodiments, at least 90% of either 1) the internal volume of the reaction chamber, or 2) a cross-section of the reaction channel. In some embodiments, a microchannel can contain a sorbent material instead, or in addition to, a catalyst In many preferred embodiments, the microchannel apparatus contains multiple microchannels, preferably groups of at least 5, more preferably at least 10, parallel channels that are connected in a common manifold that is integral to the device (not a subsequently-attached tube) where the common manifold includes a feature or features that tend to equalize flow through the channels connected to the manifold. Examples of such manifolds are described in U.S. patent application Ser. No. 10/695,400, filed Oct. 27, 2003 which is incorporated herein as if reproduced in full below. In this context, "parallel" does not necessarily mean straight, rather that the channels conform to each other. In some preferred embodiments, a microchannel device includes at least three groups of parallel microchannels wherein the channel within each group is connected to a common manifold (for example, 4 groups of microchannels and 4 manifolds) and preferably where each common manifold includes a feature or features that tend to equalize flow through the channels connected to the manifold. An aluminide coating can be formed in a group of connected microchannels by passing an aluminum-containing gas into a manifold, typically, the manifold will also be coated.

Heat exchange fluids may flow through heat transfer channels (preferably microchannels) adjacent to process channels (preferably reaction microchannels), and can be gases or liquids and may include steam, liquid metals, oils, or any other known heat exchange fluids—the system can be optimized to have a phase change in the heat exchanger. In some preferred embodiments, multiple heat exchange layers are interleaved with multiple process microchannels. For example, at least 10 heat exchangers interleaved with at least 10 process microchannels. Each of these layers may contain simple, straight channels or channels within a layer may have more complex geometries.

While simple microchannels can be utilized, the invention has advantages for apparatus with complex microchannel geometries. In some preferred embodiments, the microchannel apparatus includes one or more of the following characteristics: at least one contiguous microchannel has a turn of at least 45°, in some embodiments at least 90°, in some embodiments a u-bend, a length of 50 cm or more, or a length of 20 cm or more along with a dimension of 2 mm or less, and in some embodiments a length of 50-500 cm; at least 2 adjacent channels, having an adjacent length of at least one cm, are connected by plural orifices along a common microchannel wall where the area of orifices amounts to 20% or less of the area of the microchannel wall in which the orifices are located and where each orifice is 0.6 mm$^2$ or smaller, in some embodiments 0.1 mm$^2$ or smaller—this is a particularly challenging configuration because a coating should be applied without clogging the holes; or at least two, in some embodiments at least 5, parallel microchannels having a length of at least 1 cm, have openings to an integral manifold, where the manifold includes at least one dimension that is no more than three times the minimum dimension of the parallel microchannels (for example, if one of the parallel microchannels had a height of 1 mm (as the smallest dimension in the set of parallel microchannels), then the manifold would possess a height of no more than 3 mm). An integral manifold is part of the assembled device and is not a connecting tube. In some apparatus, a microchannel contains a u-bend which means that, during operation, flow (or at least a portion of the flow) passes in opposite directions within a device and within a contiguous channel (note that a contiguous channel with a u-bend includes split flows such as a w-bend, although in some preferred embodiments all flow within a microchannel passes through the u-bend and in the opposite direction in a single microchannel).

Electroless coatings are especially useful in integrated combustion reactors that have combustion channels coupled with endothermic reaction channels. A combustion microchannel can be straight, curved or have a complex shape. Typically, the combustion channel will be adjacent to and conformal with an endothermic reaction channel. In some embodiments, fuel and oxidant enter together at the entrance of a channel; however, this configuration can lead to a hot spot wherever the conditions are sufficient for combustion, and may even lead to detonation. In preferred embodiments, the fuel or oxidant is added in a staged fashion along the length of channel; this allows careful control of temperature profile along the length of microchannel. The temperature may rise monotonically in a linear fashion or may rise more quickly near either the front or end of the catalyst bed. In some cases the temperature profile is not monotonic, as with addition of fuel or oxidant there are local peaks in temperature, although these are usually less than 25° C. and preferably less than 10° C. more than the average local temperature measured over lengths greater than 2 mm. Thus, in some examples, the section of the catalyst-containing microchannel that exceeds 800° C. may only include the final 75%, or 50%, or 25%, or 10% of the catalyst bed, or any value therewithin. For the example of a temperature profile ranging from 650° C. to 850° C., the reaction may equilibrate near 840° C. and demonstrate an approach to equilibrium greater than 80% as defined by the peak temperature. The equivalent contact time spent in the reaction zone that exceeds 800° C. may be considerably less than the overall reaction contact time as defined by the entire reaction channel volume (i.e., the volume of the channel containing catalyst). As an example, the contact time within the entire reaction channel volume may be 5 ms, but only 1 ms in the reactor section at temperatures in the range of 800 to 850° C. In some embodiments, the temperature of the catalyst-containing microchannel may be highest near the end of the reaction zone, or, alternatively, may be higher near the front or middle of the reactor rather than near the end of the reaction zone.

In addition to combustion channel(s), additional features such as microchannel or non-microchannel endothermic reaction channels may be present. Microchannel reaction channels are preferred. Having combustion microchannels adjacent endothermic reaction channels enable temperature in the reaction channels to be controlled precisely to promote steam reforming, or other endothermic reactions, and minimize unselective reactions in the gas phase. The thickness of a wall between adjacent process channels and combustion channels is preferably 5 mm or less. Each of the process or combustion channels may be further subdivided with parallel subchannels. The flow through adjacent endothermic reaction and combustion channels may be cross flow, counter-flow or co-flow. As described in greater detail in some of the incorporated patents, in some preferred embodiments combustion channels may be formed of a fuel subchannel and a oxidant subchannel that are connected to allow the controlled mixing of fuel and oxidant (sometimes called staged addition). For example, a hydrocarbon fuel can be added at one end of a fuel subchannel and oxygen is added from an adjacent oxygen subchannel through holes along the length (typically only part of the total length) of the fuel subchannel. In some preferred embodiments, the combustion channels have a u-shape in which fuel enters one end of the "u," is combusted, and exhaust exits from the other side of the "u." In a particularly preferred embodiment, a hydrocarbon fuel such as methane further comprises hydrogen and CO (such as might become from a part of the product stream of a steam reforming reaction that is powered by the combustion reaction) and this mixture is combusted with oxygen in a first zone of a combustion channel. The hydrogen combusts quickly and a second zone of the combustion channel contains a fuel-rich mixture of hydrocarbon, CO and oxygen. A second zone (the fuel lean or exhaust zone) contains a fuel-lean mixture of hydrocarbon, CO and oxygen.

The methods, reactors, catalysts and chemical systems of the present invention can also be characterized in terms of the data presented in the Examples section. These measured properties may also be described as "about" or "at least about" or "no more than about" the values shown in the examples; it should be understood that these values are characteristic of various embodiments of the invention that can be obtained through routine experimentation in view of the descriptions herein.

In some preferred embodiments, the inventive apparatus (or method) includes a catalyst material. In preferred embodiments, the surface of the catalyst defines at least one wall of a bulk flow path through which the mixture passes. During operation, a reactant composition flows through the microchannel, past and in contact with the catalyst. In some embodiments, a catalyst is provided as an insert that can be inserted into (or removed from) each channel in a single piece; of course the insert would need to be sized to fit within the microchannel. The catalyst can also be a coating (such as a washcoat) of material within a microchannel reaction channel or channels. The use of a flow-by catalyst configuration can create an advantageous capacity/pressure drop relationship. In a flow-by catalyst configuration, fluid preferably flows in a gap adjacent to a porous insert or past a wall coating of catalyst that contacts the microchannel wall (preferably the microchannel wall in direct thermal contact with a heat exchanger (preferably a microchannel heat exchanger), and in some embodiments a coolant or heating stream contacts the opposite side of the wall that contacts the catalyst.

Metal Aluminide Layer

In some embodiments of the invention, at least a portion of at least one interior wall of a microchannel apparatus (preferably a microreactor) is coated with a layer of a metal aluminide (preferably nickel aluminide (NiAl) or platinum aluminide (PtAl)). In addition, nickel or Pt may be plated onto a metal that is not rich in nickel, such as stainless steel, to create a reactive surface for the aluminidization process. Nickel aluminide could also be deposited by supplying both Al and Ni precursors in the vapor phase concurrently or as a mixture. In a related aspect, a catalyst or catalyst intermediate can be formed on substrates having a Ni and/or Pt aluminide surface.

In preferred embodiments, nickel aluminide contains 13 to 32 wt % aluminum, more preferably 20 to 32 wt %; and still more preferably consists essentially of beta-NiAl. If Al falls significantly below the 13% weight wt % level of the gamma-prime phase, it may be expected to negatively affect the quality of the thermally-grown alumina scale.

In some embodiments, the metal aluminide layer has a thickness of 1 to 100 micrometers (μm); in some embodiments a thickness of 2 to 50 μm; and in some embodiments a thickness of 5 to 25 μm. In some embodiments, the aluminide layer is completely oxidized; however, this is generally not preferred.

Thermally Grown Oxide

Prior to electroless plating, an oxide layer can be formed by exposing a metallic surface to an oxidizing atmosphere at elevated temperature. The oxidizing gas could be air, diluted air, oxygen, $CO_2$, steam, NOx or any mixture of these gases or other gases that have substantial oxidizing power. The temperature of oxide growth is at least 500° C., preferably at least 650° C. The surface can be exposed to the treatment condition in stages of different temperatures, different oxidizing powers, or both. For example, the surface could be treated at 650° C. for a time and then heated to 1000° C. and kept at 1000° C. for an additional time. Controlled and staged surface treatment can generate a surface structure of a desired morphology and composition. Superior oxide coatings result from reheating to about 1000° C. (in some embodiments at least 900° C.) under an inert, or preferably, a reducing atmosphere such as a $H_2$-containing atmosphere (preferably at least 1000 ppm $H_2$, in some embodiments 1 to 100% $H_2$). Preheat under a reducing atmosphere was observed to produce superior oxide coatings with little or no spalling.

The thermally-grown oxide layer is preferably 10 μm thick or less, more preferably preferably 1 μm thick or less, and in some embodiments is 0.2 μm to 5 μm thick. Typically, these thicknesses are measured with an optical or electron microscope. Generally, a thermally-grown oxide layer can be visually identified; the underlying aluminide layer is metallic in nature and contains no more than 5 wt % oxygen atoms; surface layers may be distinguished from a thermally-grown oxide by differences in density, porosity or crystal phase.

It should be recognized that the term "alumina" can be used to refer to a material containing aluminum oxides in the presence of additional metals. In the descriptions herein, unless specified, the term "alumina" encompasses substantially pure material ("consists essentially of alumina") and/or aluminum oxides containing modifiers.

An aluminized surface can be modified by the addition of alkaline earth elements (Be, Mg, Ca, Sr, Ba), rare earth elements (Y, La, Ce, Pr, Nd, Pm, Sm, Eu, Gd, Tb, Dy, Ho, Er, Tm, Yb, Lu) or combinations of these. The addition of these elements is followed by a reaction with an oxidizing atmosphere to form a mixed oxide scale. When the modifying element is La, for example, the scale contains LaAlOx, lanthanum aluminate. In some embodiments, a stabilized alumina surface can be formed by adding a rare earth element such as La.

Reactions

The coated microchannel apparatus is especially useful when used with a surface catalyst and at high temperature, for example, at temperatures above 180° C., above 250° C., above 500° C., in some embodiments 700° C. or higher, or in some embodiments 900° C. or higher.

In some aspects, the invention provides a method of conducting a reaction, comprising: flowing at least one reactant into a microchannel, and reacting the at least one reactant in the presence of a catalyst within a microchannel to form at least one product. In some embodiments, the reaction consists essentially of a reaction selected from: acetylation, addition reactions, alkylation, dealkylation, hydrodealkylation, reductive alkylation, amination, ammoxidation, ammonia synthesis, aromatization, arylation, autothermal reforming, carbonylation, decarbonylation, reductive carbonylation, carboxylation, reductive carboxylation, reductive coupling, condensation, cracking, hydrocracking, cyclization, cyclooligomerization, dehalogenation, dimerization, esterification, Fischer-Tropsch, halogenation, hydrohalogenation, homologation, hydration, dehydration, hydrogenation, dehydrogenation, hydrocarboxylation, hydroformylation, hydrogenolysis, hydrometallation, hydrolysis, hydrotreating (HDS/HDN), isomerization, methylation, demethylation, metathesis, nitration, oxidation, partial oxidation, reduction, reformation, reverse water gas shift, Sabatier, selective oxidation, sulfonation, transesterification, and water gas shift. Combustion is another preferred reaction. Hydrocarbon steam reforming is especially preferred (such as methane, ethane or propane steam reforming). In some preferred embodiments, the microchannel comprises an electrolessly applied coating that serves as a passivation and/or catalyst coating.

Hydrocarbons according to the present invention include: alkanes, alkenes, alkynes, alcohols, aromatics, and combinations thereof including fuels such as gasoline, kerosene, diesel, JP-8. For purposes of the present invention, "hydrocarbons" refers to compounds containing C—H bonds that combust to produce heat; although not desirable in a combustion fuel, less preferred embodiments of a "hydrocarbon" may include, for example, alcohols; since these can be combusted. Preferably, the hydrocarbon is an alkane. Preferred alkanes are $C_1$-$C_{10}$ alkanes, such as methane, ethane, propane, butane, and isooctane. In some embodiments, the hydrocarbon comprises methane, ethane, propane, butane, or combinations of these. A preferred oxidant is oxygen which, in some preferred embodiments, is in the form of air.

In some preferred embodiments, gas hourly space velocity (GHSV) of the inventive methods may range from 1,000 $h^{-1}$ to 10,000,000 $h^{-1}$ based on reactor volume, or 1,000 ml feed/(g catalyst)(hr) to 10,000,000 ml feed/(g catalyst)(hr). In other preferred embodiments, GHSV is at least 10,000 $h^{-1}$ or at least 10,000 ml feed/(g catalyst)(hr); more preferably at least 100,000 $h^{-1}$ or at least 100,000 ml feed/(g catalyst)(hr); more preferably at least 500,000 $h^{-1}$ or at least 500,000 ml feed/g catalyst; more preferably at least 1,000,000 $h^{-1}$ or at least 1,000,000 ml feed/(g catalyst)(hr).

The present invention may include methods of combustion in which a hydrocarbon is reacted with oxygen at short residence times (or alternatively, described in contact times) over the catalysts described herein. The residence time is preferably less than 0.1 s. In some embodiments, short hydrocarbon contact times are preferably 5-100 milliseconds (msec), in some embodiments, less than 25 msec in a zone.

Combustion reactions are preferably carried out at more than 650° C., more preferably more than 750° C., and in some embodiments in the range of 675 to 900° C. The reaction can be run over a broad pressure range from sub-ambient to very high, in some embodiments the process is conducted at a pressure of from 1 atm to 10 atm, more preferably 1 atm to 2 atm. In some preferred embodiments, where oxidant (typically oxygen that may be pure, or in the form of air, or in another mixture) is added along the length of a combustion channel, the combustion reaction conditions can be described as having two zones: an initial, fuel-rich zone (that may also contain $H_2$ and CO); and a fuel lean zone called the afterburner zone. Typically, these zones are not distinct, but the fuel-rich zone gradually changes into the fuel lean zone. Fuel compositions in these zones are described at the start of a zone.

Certain aspects of the invention can best be described in terms of properties such as stability, conversion or selectivity. Both the catalysts and methods can be characterized in terms of hydrocarbon conversions and selectivities in combustion processes. Hydrocarbon conversion is preferably at least 50%, more preferably at least 80% and still more preferably at least 90%. The foregoing conversion values can be either absolute or equilibrium conversions. If not specified, conversion refers to absolute conversion. Under conditions where conversion approaches 100% (as is the case in oxygen-rich, fuel-lean environments), absolute and equilibrium conversion is the same. "Equilibrium conversion" is defined in the classical manner, where the maximum attainable conversion is a function of the reactor temperature, pressure, and feed composition. In some embodiments, hydrocarbon equilibrium conversion is in the range of 70 to 100%. Hydrocarbon can be a mixture of hydrocarbons, or, in some embodiments, the term "hydrocarbon" could be replaced by "methane" in any of the descriptions herein. In the descriptions of preferred parameters for a multizone combustion process, the amounts of "hydrocarbon" (or contact time of hydrocarbon) are based on methane and it should be understood that for heavier fuels the flow rate would be reduced proportionately based on the conversion to $CO_2$ and $H_2O$; for example, for ethane the flow rate should be adjusted considering the stoichiometric ratio of oxygen to ethane now is 3.5 rather than 2.0 for oxygen to methane. So, if a patent claim states "a flow rate of 1.0 cc hydrocarbon", this means a flow rate of 1.0 cc methane or 0.57 cc ethane, etc.

In the fuel-rich zone, the maximum temperature is preferably 850° C. or less, more preferably 800° C. or less, and in some embodiments the temperature is in the range of 670° C.

to 800° C. In some embodiments, the partial pressure of $H_2$ is preferably at least 0.02 atm, in some embodiments in the range of 0.11 to 0.27 atm. In some embodiments, the partial pressure of hydrocarbon is CO is preferably at least 0.03 atm, in some embodiments in the range of 0.04 to 0.1 atm. The partial pressure of hydrocarbon is preferably at least 0.071 atm, in some embodiments in the range of 0.064 to 0.16 atm. In some embodiments, mole fractions of hydrocarbon, $H_2$, CO, and $O_2$ are in the range of 0.01-0.08, 0.02-0.13, 0.03-0.05 and 0.1-0.12. Contact time of fuel (including both $H_2$ and hydrocarbon) in the fuel rich zone is preferably 5 msec or less, more preferably 2.8 msec or less, and in some embodiments is in the range of 2 to 5 msec. Contact time of hydrocarbon in the fuel rich zone is preferably less than 200 msec, more preferably 40 msec or less, more preferably 20 msec or less, and in some embodiments in the range of 5 to 20 msec. Conversion of hydrocarbon in the fuel rich zone is preferably at least 40%, more preferably at least 50%, and in some embodiments 40 to 60%. In some embodiments, relative amounts (by mole) of various components entering the fuel rich zone are 50-100 parts hydrocarbon, 35-60 parts CO, 120-150 parts $H_2$, and 80-140 parts $O_2$, and in some embodiments, 60-90 parts hydrocarbon, 35-60 parts CO, 100-150 parts $H_2$, and 100-120 parts $O_2$. Through the fuel rich zone, the hydrocarbon conversion is preferably at least 40%, in some embodiments 40 to about 70%, $O_2$ conversion is preferably at least 30%, oxygen selectivity to $H_2O$ is preferably 80% or less, more preferably less than 75%, and the oxygen selectivity of hydrocarbon to CO is the same or greater than the oxygen selectivity of CO to $CO_2$. For purposes of defining selectivity, $O_2$ is assumed to be used for converting CO to $CO_2$, $CH_4$ to CO and $H_2$, $H_2$ to $H_2O$, and $CH_4$ to $H_2O$. The percent of $O_2$ used to selectively oxidize each of above mentioned compounds is calculated as $O_2$ selectivity.

Defining [(exit flow rate $CO_2$)+(inlet flow rate methane–exit flow rate methane)+(exit flow rate $H_2O$)]=A $O_2$ selectivity to CO=(exit flow rate $CO_2$)×100%/A $O_2$ selectivity to $H_2O$=(exit flow rate $H_2O$)×100%/A $O_2$ selectivity $CH_4$ to CO=(inlet flow rate methane–exit flow rate methane)×100%/A In the fuel lean zone, the maximum temperature is preferably 920° C. or less, in some embodiments 850° C. or less, and in some embodiments the maximum temperature is in the range of 750 to 900° C. The partial pressure of CO entering the fuel lean zone is preferably at least 0.02 atm, in some embodiments in the range of 0.015 to 0.045 atm. The partial pressure of hydrocarbon entering the fuel lean zone is preferably at least 0.006 atm, in some embodiments in the range of 0.005 to 0.015 atm. In some embodiments, mole fractions of hydrocarbon, $H_2$, CO, and $O_2$ are preferably in the range of 0.005-0.007, 0.006-0.008, and 0.04-0.05, respectively. In some embodiments, contact time of fuel in the fuel lean zone is preferably at least 3.0 times that of the $H_2$/CO zone, preferably 1 sec or less, more preferably 500 msec or less, and in some embodiments is in the range of 50-500 msec. In some embodiments, relative amounts (by mole) of various components entering the fuel lean zone are 1-20 parts hydrocarbon, 10-50 parts CO, 0-20 parts $H_2$, and 20-100 parts $O_2$, and in some embodiments, 2-10 parts hydrocarbon, 10-30 parts CO, 0-10 parts $H_2$, and 30-60 parts $O_2$. Conversion of hydrocarbon in the fuel lean zone is preferably at least 93%, more preferably at least 95%, more preferably at least 99%, and in some embodiments 93 to 100%. Conversion of CO in the fuel lean zone is preferably at least 93%, more preferably at least 95%, more preferably at least 99%, and in some embodiments 93 to 100%.

The amounts of gases in each zone refer to components entering a zone. So the simplest case would be where all the components enter a zone together; however, one or more components could also be added in a distributed fashion along the length of a zone, or be added mid-zone, etc., and these would also be counted as entering the zone.

In some preferred embodiments, a catalyst is characterizable by the levels of stability and/or reactivity shown in the examples.

Surface Features in Microchannel Walls

In some preferred embodiments, apparatus contains channels having surface features to enhance fluid contact with a catalyst and/or channel walls. Surface features are protrusions from or recesses into a channel wall. If the area at the top of the features is the same or exceeds the area at the base of the feature, then the feature may be considered recessed. If the area at the base of the feature exceeds the area at the top of the feature, then it may be considered protruded. Surface features are described in detail in U.S. patent application Ser. No. 11/388,792, filed Mar. 23, 2006, which is incorporated herein as if reproduced in full below. The staggered herringbone configuration is a particularly well-known configuration for surface features.

Preferred ranges for surface feature depth (as defined as recessed or protruded distance normal to the direction of flow through a channel) are less than 2 mm. More preferably less than 1 mm. In some embodiments from 0.01 mm to 0.5 mm. The preferred range for the width of the surface feature (as defined as the open distance parallel to the direction of gravity) is less than 2 mm. More preferably less than 1 mm. In some embodiments from 0.1 to 0.5 mm.

The length and width of a surface feature are defined in the same way as for a microchannel. The depth is the distance which the feature sinks into the microchannel surface; it is the same direction as microchannel height and microchannel gap. In one preferred embodiment, comprising a stacked and bonded device with surface features on the sheet surfaces, the surface feature depth corresponds to the direction of stacking. These dimensions of the surface features refer the maximum dimension of a feature; for example the depth of a rounded groove refers to the maximum depth, that is, the depth at the bottom of the groove.

An advantage of electroless plating is that essentially uniform coatings can be formed on surface features within a microchannel. Measuring coating thickness is performed ex situ by cutting the device into cross sections and taking SEM photographs to quantitatively measure the coating thickness.

EXAMPLES

Pt Electroless Coating

Example 1

A Ni-aluminide coupon (0.01 in×0.35 in×1 in) was heated to 1050° C. in flowing $H_2$ at 3.5° C./min heating rate. After purging with Ar for 1 hour at 1050° C., the gas is changed to 21% $O_2$/Ar. The coupon was heat-treated in flowing $O_2$/Ar for 10 hours and then cooled to room temperature. An $\alpha$-$Al_2O_3$ scale was generated on the surface after the heat treatment.

A solution consisting of $Pt(NH_3)_4(NO_3)_2$ (0.2 wt % Pt) and 0.2 wt % $N_2H_4 \cdot H_2O$ was prepared. The heat-treated coupon was put into the solution with stirring. The plating was performed at 60° C. for 7 hours. Subsequently, the coupon is rinsed with water and dried with blowing air. Around 2.2 mg/in² of Pt was plated on the surface.

Example 2

A solution containing Pt(NH$_3$)$_4$(OH)$_2$ (0.2 wt % Pt) and 0.2 wt % N$_2$H$_4$H$_2$O was prepared. An alloy 617 coupon (0.01 in×0.35 in×1 in) was hung in the solution at room temperature. The solution was stirred for 24 hours. Subsequently, the coupon was rinsed with water and dried with blowing air. The weight gain of the coupon was 8.5 mg/in².

Example 3

A Ni-aluminide coupon (0.02 in×0.2 in×1 in) was heated to 1050° C. in flowing H$_2$ at 3.5° C./min heating rate. After purging with Ar for 1 hour at 1050° C., the gas was changed to 21% O$_2$/Ar. The coupon was heat-treated in following O$_2$/Ar for 10 hours and then cooled to room temperature. An α-Al$_2$O$_3$ scale is generated on the surface after the heat treatment.

The coupon was hung in a solution containing 0.2 wt % Pt as Pt(NH$_3$)$_4$(OH)$_2$ and 0.2 wt % NaBH$_4$ at room temperature. The solution was stirred for 5 hours. Subsequently, the coupon was rinsed with water and dried with blowing air. The weight gain of the coupon was 4.8 mg/in².

Example 4

A solution consisting of Pt(NH$_3$)$_4$(NO$_3$)$_2$, (10 g/L Pt), 10 g/L N$_2$H$_4$.H$_2$O and acetic acid was prepared. The pH value of the solution was adjusted to 5.8 by acetic acid. An aluminized alloy 617 was heat-treated at 1050° C. for 10 hours. The surface of the coupon was covered with an α-Al$_2$O$_3$ scale. The coupon was put in the solution for 12 hours at 80-85° C. Around 28 mg/in² of Pt was plated on the surface. Next, the Pt-plated coupon was calcined at 1000° C. for 4 hours. The SEM micrographs of the Pt-plated coupon are shown in FIG. 1. The Pt crystal size is from around 0.2 micron to 1.5 microns.

Example 5

Electroless Plating in Complex Microchannels

A microchannel device was used to demonstrate the effectiveness of electroless plating of platinum. The device has two microchannels in parallel, in communication via a series of small holes (0.016-0.050 inch in diameter) along the channel length. Channel A has a total length of 24 inches and a cross section of 0.160 inch by 0.050 inch. It is of a U design with each arm of the U being 12 inch long. Channel B has a length of 6 inch and a cross section of 0.160 inch by 0.050 inch. An access is provided at the U for introduction of solution for electroless plating.

Electroless plating was done by filling the channels with a solution of (NH$_3$)$_4$Pt(OH)$_2$ (5 wt % Pt) and hydrazine (5 wt %) in DI water at room temperature, letting the solution sit in the device for 20 hours, and followed by draining, rinsing, drying and final calcination at 450 C for 4 hr. The device was then autopsied and examined by optical and electron microscopies. It was found for the portion of the channels filled with the solution, the channel walls were well coated with platinum of at least 1 micron in thickness. The coating was uniform even at the U-turn and around the holes.

Example 6

A Ni-aluminide coupon (1"×0.35"×0.02") was heat-treated at 1050° C. for 10 hours prior to use. The surface of the coupon was covered with an α-Al$_2$O$_3$ scale. The coupon was then put in a solution consisting of Pt(NH$_3$)$_4$(OH)$_2$, (0.2 wt % Pt) and 0.2 wt % N$_2$H$_4$.H$_2$O. The plating was performed at room temperature for 8 hours. The Pt loading was 5.0 mg/in². 10 g 28-30 wt % NH$_3$.H$_2$O solution and 1.1 g RhCl$_3$.xH$_2$O were mixed in a glass bottle with stirring. The mixture is heated to 60-100° C. with an oil bath. The temperature was kept at 60-100° C. till the solvent is vaporized. A yellow powder Rh(NH$_3$)$_x$Cl$_3$ was obtained. 1.34 g Rh(NH$_3$)$_x$Cl$_3$ and 134 g H$_2$O were mixed in a beaker with stirring. Subsequently 2.75 g Amberlite IRA-410 ion-exchange resin was added for exchanging Cl⁻ to OH⁻. The mixture was heated at 80° C. for 1 hour. The solution was separated from the resin by filtration to obtain a Rh(NH$_3$)$_x$(OH)$_3$ solution. 0.66 g 28-30 wt % NH$_3$.H$_2$O solution and 5.34 g Rh(NH$_3$)$_x$(OH)$_3$ solution were mixed in a glass bottle. 1.2 g hydrazine hydrate was then added. Subsequently, the Pt-plated coupon was put in the solution at room temperature for 2 days. The Rh loading was 3.3 mg/in².

Example 7

10 g 28-30 wt % NH$_3$.H$_2$O solution and 1.1 g RhCl$_3$.xH$_2$O were mixed in a glass bottle with stirring. The mixture was heated to 60-100° C. with an oil bath. The temperature was kept at 60-100° C. till the solvent was vaporized. A yellow powder Rh(NH$_3$)$_x$Cl$_3$ was obtained. 1.34 g Rh(NH$_3$)$_x$Cl$_3$ and 134 g H$_2$O were mixed in a beaker with stirring. Subsequently 2.75 g Amberlite IRA-410 ion-exchange resin was added for exchanging Cl⁻ to OH⁻. The mixture was heated at 80° C. for 1 hour. The solution was separated from the resin by filtration. The ion-exchange process was repeated once. A Rh(NH$_3$)$_x$(OH)$_3$ solution formed. 5 g Rh(NH$_3$)$_x$(OH)$_3$ solution and 0.1 g Pt(NH$_3$)$_4$(OH)$_2$ solution (9.09 wt % Pt) were mixed in a glass bottle. 1 g hydrazine hydrate is added. Subsequently, a heat-treated NiAl coupon was put in the solution. The solution was heated to 60° C. for 4 hours. The resulting Pt—Rh loading was 2.7 mg/in².

Example 8

10 g 28-30 wt % NH$_3$.H$_2$O solution and 1.1 g RhCl$_3$.xH$_2$O were mixed in a glass bottle with stirring. The mixture is heated to 60-100° C. with an oil bath. The temperature was kept at 60-100° C. till the solvent vaporized. A yellow powder Rh(NH$_3$)$_x$Cl$_3$ was obtained. 1.34 g Rh(NH$_3$)$_x$Cl$_3$ and 134 g H$_2$O were mixed in a beaker with stirring. Subsequently 2.75 g Amberlite IRA-410 ion-exchange resin was added for exchanging Cl⁻ to OH⁻. The mixture was heated at 80° C. for 1 hour. The solution was separated from the resin by filtration. The ion-exchange process was repeated once. A Rh(NH$_3$)$_x$(OH)$_3$ solution formed. 4 g Rh(NH$_3$)$_x$(OH)$_3$ solution and 1 g hydrazine hydrate were mixed in a glass bottle with stirring. Subsequently, 0.1 g 10 wt % MgO—Al$_2$O$_3$ powder was added to the solution. The plating was performed at room temperature for 4 days resulting in a Rh/10% MgO—Al$_2$O$_3$ powder.

Example 9

A Ni-aluminide coupon (1"×0.35"×0.01") was heat-treated at 1050° C. for 10 hours prior to use. The surface of the coupon was covered with an α-Al$_2$O$_3$ scale. The coupon was then put in a solution consisting of Pt(NH$_3$)$_4$(OH)$_2$, (0.2 wt % Pt) and 0.2 wt % N$_2$H$_4$.H$_2$O. The plating was performed at room temperature for 24 hours. The Pt loading was 9.0 mg/in². 10 g 28-30 wt % NH$_3$.H$_2$O solution and 3.0 g Rh(NO$_3$)$_3$ solution (10 wt % Rh) were mixed in a glass bottle with stirring. The mixture was heated to 80° C. for 30 min and then cooled to room temperature. Next the slurry is filtered to obtain a yellow powder $Rh(NH_3)_x(NO_3)_3$. 0.04 g $Rh(NH_3)_x(NO_3)_3$ and 19 g $H_2O$ were mixed in a glass bottle with stirring. The mixture was heated to 60° C. for 30 min and then cooled to room temperature. 1.0 g hydrazine hydrate was added. Subsequently, the Pt-plated coupon is put in the solution at room temperature for 2 days. The Rh loading was 1.4 mg/in².

Example 10

10 g of a 28-30 wt % $NH_3.H_2O$ solution and 1.1 g of $RhCl_3.xH_2O$ were mixed in a glass bottle with stirring. The mixture was heated to 60-100° C. in an oil bath. The temperature was kept at 60-100° C. until the solvent was vaporized. A yellow powder $Rh(NH_3)_xCl_3$ was obtained. 1.34 g of $Rh(NH_3)_xCl_3$ and 134 g of $H_2O$ were mixed in a beaker with stirring. Subsequently 2.75 g Amberlite IRA-410 ion-exchange resin was added for exchanging Cl⁻ to OH⁻. The mixture was heated at 80° C. for 1 hour. The solution was separated from the resin by filtration. The ion-exchange process was repeated once. A $Rh(NH_3)_x(OH)_3$ solution was formed. 0.5 g of a 28-30 wt % $NH_3.H_2O$ solution and 4.5 g of a $Rh(NH_3)_x(OH)_3$ solution were mixed in a glass bottle. 1.0 g of hydrazine hydrate was then added. Subsequently, a Pt—Rh plated NiAl coupon (5 mg/in² Pt and 3 mg/in² Rh) was put in the solution at room temperature for 22 hrs. The Rh loading was 0.4 mg/in² (Table 1).

Example 11

2 ppm $CuCl_2$ was added to a Rh plating bath with the same composition as that in example 10. Subsequently, a Pt—Rh plated NiAl coupon (5 mg/in² Pt and 3 mg/in² Rh) was put in the solution at room temperature for 22 hrs. The Rh loading was 0.6 mg/in² (Table 1). The Rh plating rate increased by 50% as compared with that without Cu (Example 10).

Example 12

20 ppm of $CuCl_2$ was added to a Rh plating bath with the same composition as that in example 10. Subsequently, a Pt—Rh plated NiAl coupon (5 mg/in² Pt and 3 mg/in² Rh) was put in the solution at room temperature for 22 hrs. The Rh loading was 0.8 mg/in² (Table 1). The Rh plating rate is increased by 100% as compared with that without Cu (Example 10).

Example 13

20 ppm of $Pb(CH_3COO)_2$ was added to a Rh plating bath with the same composition as that in example 10. Subsequently, a Pt—Rh plated NiAl coupon (5 mg/in² Pt and 3 mg/in² Rh) was put in the solution at room temperature for 22 hrs. The Rh loading was 0.6 mg/in² (Table 1). The Rh plating rate is increased by 50% as compared with that without Pb (Example 10).

TABLE 1

Effect of Cu and Pb on Rh plating rate

| No. | Solution | Coupon | Time (h) | Rh loading (mg/in²) |
|---|---|---|---|---|
| 1 | w/o $CuCl_2$ | 5Pt—3Rh/NiAl | 22 | 0.4 |
| 2 | 2 ppm $CuCl_2$ | 5Pt—3Rh/NiAl | 22 | 0.6 |
| 3 | 20 ppm $CuCl_2$ | 5Pt—3Rh/NiAl | 22 | 0.8 |
| 4 | 20 ppm $PbAc_2$ | 5Pt—3Rh/NiAl | 22 | 0.6 |

Combustion testing of electrolessly plated Pt—Rh catalyst

Example 14

Preparation of Electrolessly Plated Pt—Rh Catalyst

A Ni-aluminide coupon (0.02 in×0.372 in×1 in) was heated to 1050° C. in flowing $H_2$ at 3.5° C./min heating rate. After purging with Ar for 1 hour at 1050° C., the gas was changed to 21% $O_2$/Ar. The coupon was heat-treated in following $O_2$/Ar for 10 hours and then cooled to room temperature. An α-$Al_2O_3$ scale was generated on the surface after the heat treatment. The coupon was hung in 50 g $Pt(NH_3)_4(OH)_2$ solution containing 0.2 wt % Pt and 0.2 wt % $N_2H_4H_2O$ at room temperature. The solution was stirred overnight. After that, the coupon was rinsed with water and dried with blowing air. The weight gain of the coupon was 7.1 mg/in². The coupon was then put in a new Pt solution with the same composition with stirring. After 4-hour plating, the coupon was rinsed with water, dried and then calcined at 450° C. for 0.5 hour. The total Pt loading was 15 mg/in².

$Rh(NH_3)_x(NO_2)_y$ solution for electroless Rh plating was prepared as follows. 0.5 g $RhCl_3.xH_2O$ was dissolved in 100 ml $H_2O$ to form a red solution. After 10 g $NaNO_2$ was added, the solution was heated to the boiling point (around 98° C.) and kept for 30 min. The color of the solution changed to light yellow. After cooling to room temperature, 25 ml 5 mol/L $NH_3.H_2O$ solution was added. The solution was stirred for additional 1 hour to form $Rh(NH_3)_x(NO_2)_y$ solution. The above Pt plated coupon was put into 20 g $Rh(NH_3)_x(NO_2)_y$ solution and then 0.5 g $N_2H_4.H_2O$ was added for reducing the rhodium. The plating process was performed at room temperature for one day. The coupon was then rinsed with water and dried. The plating process was repeated until 10 mg/in² Rh loading was achieved.

Combustion Testing

Catalyst coupon was tested in a two inch long microreactor. The reactor is made from a 0.5" OD alloy 617 rod which is 2" long. A slot sized 0.377"×0.021"×2" was cut at the center to fit the catalyst coupon and another slot adjacent to the insert is EDM (electro discharge machining) wire cut at 0.335"×0.01"×2" for reactant gases to flow by the catalyst insert. The catalyst was tested under fuel-rich combustion conditions. The gas compositions are summarized in Table 2. $CH_4$ conversions were 31-51% under various conditions (Table 2). The catalyst did not lost its activity in 360 hrs on stream.

TABLE 2

Testing conditions and results

| | Run plan | | | | | |
|---|---|---|---|---|---|---|
| | 1 | 2 | 3 | 4 | 5 | 6 |
| Temperature (° C.) | 675 | 725 | 800 | 775 | 775 | 800 |
| CH4 flow rate (sccm) | 77 | 77 | 77 | 46 | 28 | 19 |
| CO flow rate (sccm) | 48 | 48 | 48 | 61 | 61 | 55 |
| H2 flow rate (sccm) | 136 | 136 | 136 | 78 | 50 | 34 |

TABLE 2-continued

Testing conditions and results

| | \multicolumn{6}{c}{Run plan} | | | | | |
|---|---|---|---|---|---|---|
| | 1 | 2 | 3 | 4 | 5 | 6 |
| Steam flow rate (sccm) | 0 | 0 | 0 | 124 | 187 | 212 |
| Air flow rate (sccm) | 567 | 567 | 567 | 303 | 203 | 162 |
| N2 flow rate (sccm) | 265 | 265 | 265 | 601 | 799 | 929 |
| CH4 Conversion % | 31 | 36 | 51 | 32 | 35 | 41 |

Example 15

Catalyst Preparation

A solution consisting of $Pt(NH_3)_4(OH)_2$, (2 g/L Pt) and 2 g/L $N_2H_4.H_2O$ was prepared. The pH value of the solution was 12. An aluminized alloy 617 coupon was heat-treated at 1050° C. for 10 hours before use. The surface of this coupon was covered by an $\alpha-Al_2O_3$ scale. The plating was performed at room temperature for one day. The weight gain was 12 mg/in². The plated Pt catalyst was calcined at 1000° C. for 4 hours.

Catalyst Testing

The fresh catalyst was tested in a single channel reactor for oxidative dehydrogenation of ethane to ethylene. The reactor has two microchannels separated by the catalyst coupon. Reactants were fed at 3:2:1 ratio of ethane:hydrogen:oxygen. Catalyst entrance temperature ranged from 850 to 900° C., and contact time was fixed at 40 ms. Reaction products, i.e., ethylene, acetylene, methane, propane, propylene, butylenes, butanes, CO and $CO_2$, were analyzed with an on-line four-column GC.

Catalyst Activation

After the testing, the same catalyst was activated by a redox process. The catalyst was first reduced at 850° C. for one hour in flowing 10% $H_2/N_2$ (100 SCCM). Subsequently, the gas was changed to $N_2$ for 10 min and then to 10% $O_2/N_2$ for another 1 hour at the same temperature. The redox process was repeated twice. After the activation process, the catalyst was reduced at 850° C. and submitted to ODH testing.

Results

Figure 2:
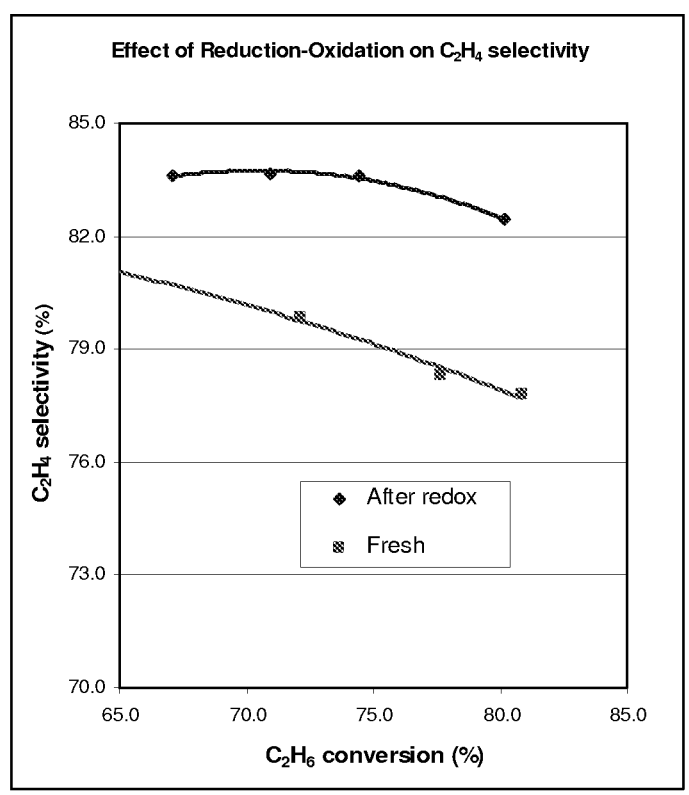
FIG. 2 shows ODH performance of an electroless plated Pt catalyst before and after redox treatment.
Figure 3:
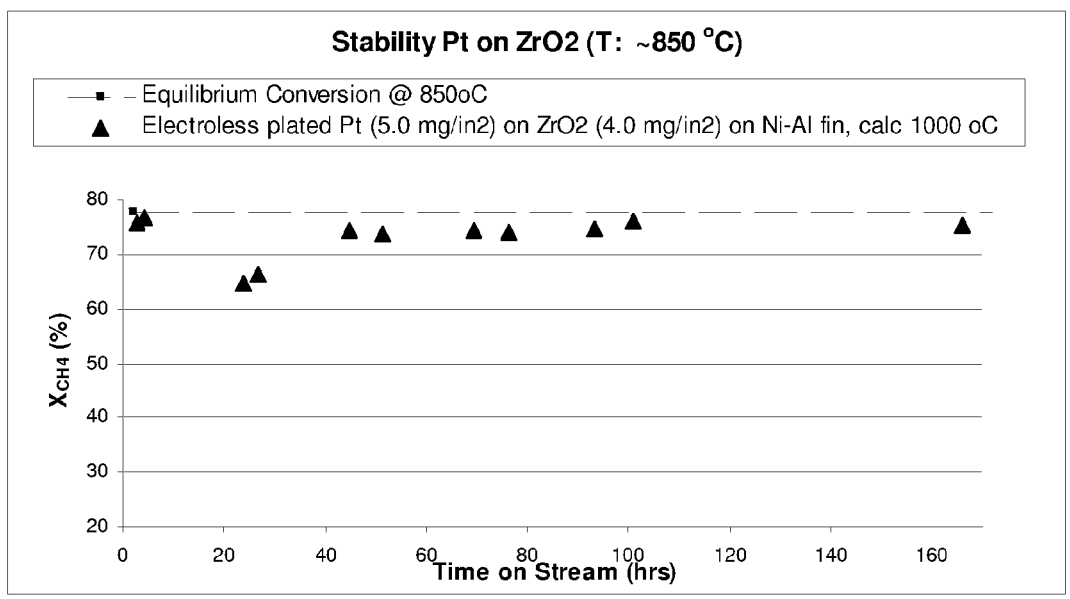
FIG. 3 shows methane conversion as a function of time for a steam methane reforming reaction in contact with a Pt—$ZrO_2$/Fin.

The performances of the electroless plated Pt catalyst before activation and after activation are shown in FIG. 2. It is observed that ethylene selectivity was improved significantly at the same ethane conversion levels after the activation process. Meanwhile, by-product CO selectivity was decreased by 2-4%. Methane selectivity was decreased by around 1%. There was not much change in the selectivities to other products, such as $C_2H_2$, $C_3H_6$, $C_3H_8$, $C_4H_8$ and $C_4H_{10}$.

Example 16

Catalyst Preparation

A Ni-aluminide fin was heated to 1050° C. in flowing $H_2$ at 3.5° C./min heating rate. The dimensions of the finned substrate are described in U.S. Published Patent Application No. 20040266615. After purging with Ar for 1 hour at 1050° C., the gas was changed to 21% $O_2$/Ar. The coupon was heat-treated in following $O_2$/Ar for 10 hours and then cooled to room temperature. An $\alpha-Al_2O_3$ scale was generated on the surface after the heat treatment. Subsequently, 10 wt % ZrO$(NO_3)_2$ solution was dropped onto the fin and dried at 80° C. for 1 hour. The coated fin was calcined at 1000° C. for 4 hours in air. The $ZrO_2$ loading is 4.2 mg/in².

The $ZrO_2$-coated fin was then put into a solution containing 0.2 wt % Pt as $Pt(NH_3)_4(NO_3)_2$ and 0.2 wt % $N_2H_4.H_2O$. The plating was performed at 60° C. for 6.5 hours. A uniform Pt layer was plated on the fin, with a loading of 5.1 mg/in². Finally the Pt—$ZrO_2$/fin was calcined at 1000° C. for 4 hours in air.

The Pt—$ZrO_2$/fin was loaded into a pellet reactor and first reduced at 450° C. for 2 hrs in 10% $H_2$ in balance $N_2$. The reaction was started at 27 atm, pellet skin temperature of 880° C. and calculated fin temperature of 856° C. Steam to carbon ratio was 3 to 1, contact time was 4.2 ms. There was an initial drop of methane conversion at 22 hrs but activity was recovered and constant at near 850° C. equilibrium conversion.

After the testing, the Pt—$ZrO_2$/fin catalyst was removed out from the pellet. There was no apparent weight loss or coke formation. This indicates that the adhesion between the Pt—$ZrO_2$ and the fin is good and the catalyst is resistant to coke formation under the testing conditions.

What is claimed:

1. A method of partially oxidizing a hydrocarbon, comprising:
    passing a process stream comprising a hydrocarbon and oxygen through a flow path at a temperature of at least 750° C. and a contact time of 10 ms or less;
    wherein the flow path is defined by channel walls;
    wherein at least one of the channel walls comprises a wall catalyst coating;
    wherein the wall catalyst coating comprises at least 3 mg/in² Rh and at least 3 mg/in² Pt; and
    converting at least 80% of the oxygen and at least 10% of the hydrocarbon in the process stream and forming CO and water.

2. The method of claim 1 comprising operating the reaction for at least 500 continuous hours without regeneration, and further wherein the catalyst maintains essentially constant activity over the at least 500 hours of operation without regeneration.

3. The method of claim 2 wherein the wall catalyst coating comprises at least 5 mg/in² Rh and at least 5 mg/in² Pt and more than 15 mg/in² (Pt+Rh).

4. The method of claim 1 wherein the hydrocarbon comprises methane, and methane conversion is at least about 75%.

5. The method of claim 4 wherein the temperature is 800° C. or less and the partial pressure of hydrocarbon is at least 0.071 atm.

6. The method of claim 1 wherein the wall catalyst coating comprises at least 5 mg/in² Rh and at least 5 mg/in² Pt and more than 15 mg/in² (Pt+Rh).

7. The method of claim 1 wherein the wall catalyst coating comprises at least 0.6 mg/cm² Rh.

8. The method of claim 1 wherein the wall catalyst coating is disposed on a metallic insertable substrate.

9. The method of claim 8 wherein the substrate has a height of less than 5 mm.

10. The method of claim 1 wherein the wall catalyst coating is disposed on a metallic substrate; wherein the metallic substrate comprises a layer of a metal aluminide.

11. The method of claim 10 further comprising a thermally grown oxide layer disposed on the metal aluminide.

12. The method of claim 1 wherein the process stream comprises 50-100 parts hydrocarbon, 35-60 parts CO, 120-150 parts $H_2$, and 80-140 parts $O_2$.

13. The method of claim 1 wherein the channel is a microchannel and wherein the catalyst coating is contiguous over at least 5 cm of the microchannel.

14. The method of claim 1 where the oxygen selectivity of hydrocarbon to CO is the same or greater than the oxygen selectivity of CO to CO2.

15. The method of claim 1 wherein the wall catalyst coating comprises more than 10 mg/in$^2$ (Pt+Rh).

16. The method of claim 15 wherein a hydrocarbon fuel is added at one end of a fuel subchannel and oxygen is added from an adjacent subchannel through holes along the length of the fuel subchannel, and further wherein the wall catalyst coating was formed by electroless plating.

17. A method of combusting a hydrocarbon comprising conducting the partial oxidation of claim 1 in a fuel rich zone followed by combustion in a fuel lean zone.

18. The method of claim 17 wherein contact time of hydrocarbon in the fuel rich zone is in the range of 2 to 5 msec.

19. The method of claim 17 wherein the fuel rich zone comprises $H_2$ and wherein the partial pressure of $H_2$ is in the range of 0.11 to 0.27 atm.

\* \* \* \* \*

UNITED STATES PATENT AND TRADEMARK OFFICE
CERTIFICATE OF CORRECTION

| | | |
|---|---|---|
| PATENT NO. | : 8,648,006 B2 | Page 1 of 1 |
| APPLICATION NO. | : 11/549625 | |
| DATED | : February 11, 2014 | |
| INVENTOR(S) | : Daly et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1849 days.

Signed and Sealed this
Fourteenth Day of April, 2015

Michelle K. Lee
*Director of the United States Patent and Trademark Office*